US011242373B2

(12) United States Patent
Thennati et al.

(10) Patent No.: US 11,242,373 B2
(45) Date of Patent: Feb. 8, 2022

(54) GLP-1 ANALOGUES

(71) Applicant: Sun Pharmaceutical Industries Limited, Maharashtra (IN)

(72) Inventors: Rajamannar Thennati, Gujarat (IN); Nishith Chaturvedi, Gujarat (IN); Vinod Sampatrao Burade, Gujarat (IN); Pradeep Dinesh Shahi, Gujarat (IN); Muthukumaran Natarajan, Gujarat (IN); Ravishankara Madavati Nagaraja, Gujarat (IN); Rishit Mansukhlal Zalawadia, Gujarat (IN); Vipulkumar Shankarbhai Patel, Gujarat (IN); Kunal Pandya, Gujarat (IN); Brijeshkumar Patel, Gujarat (IN); Dhiren Rameshchandra Joshi, Gujarat (IN); Krunal Harishbhai Soni, Gujarat (IN); Abhishek Tiwari, Gujarat (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 16/985,207

(22) Filed: Aug. 4, 2020

(65) Prior Publication Data

US 2020/0362007 A1 Nov. 19, 2020

Related U.S. Application Data

(63) Continuation of application No. 16/376,190, filed on Apr. 5, 2019.

(30) Foreign Application Priority Data

Apr. 5, 2018 (IN) ............................ 201821013109
Oct. 26, 2018 (IN) ............................ 201821040468
Oct. 26, 2018 (IN) ............................ 201821040474

(51) Int. Cl.
*A61K 38/04* (2006.01)
*C07K 14/605* (2006.01)
*A61K 9/00* (2006.01)
*A61P 3/10* (2006.01)
*A61P 3/04* (2006.01)
*A61K 38/00* (2006.01)

(52) U.S. Cl.
CPC .......... *C07K 14/605* (2013.01); *A61K 9/0053* (2013.01); *A61P 3/04* (2018.01); *A61P 3/10* (2018.01); *A61K 38/00* (2013.01)

(58) Field of Classification Search
None
See application file for complete search history.

(56) References Cited

U.S. PATENT DOCUMENTS

| | | | | |
|---|---|---|---|---|
| 6,268,343 B1 * | 7/2001 | Knudsen | .............. | C11D 3/0063 514/4.8 |
| 6,620,910 B1 | 9/2003 | Calas | | |
| 6,849,708 B1 | 2/2005 | Habener | | |
| 7,084,243 B2 | 8/2006 | Glaesner | | |
| 7,291,594 B2 | 11/2007 | Hayashi | | |
| 7,482,321 B2 | 1/2009 | Glaesner | | |
| 7,893,017 B2 | 2/2011 | Lau | | |
| 7,897,566 B2 | 3/2011 | Dong | | |
| 8,603,972 B2 | 12/2013 | Lau | | |
| 8,648,041 B2 | 2/2014 | Garibay | | |
| 8,951,959 B2 | 2/2015 | Wang | | |
| 9,006,178 B2 | 4/2015 | Kofoed | | |
| 9,266,940 B2 | 2/2016 | Wieczorek | | |
| 9,498,534 B2 | 11/2016 | Reedtz-Runge | | |
| 9,708,383 B2 | 7/2017 | Madsen | | |
| 9,758,560 B2 | 9/2017 | Lau | | |
| 9,896,495 B2 | 2/2018 | Riber et al. | | |
| 10,883,132 B2 * | 1/2021 | Nuijens | .................. | C07K 1/026 |
| 2004/0053370 A1 | 3/2004 | Glaesner | | |
| 2015/0133374 A1 | 5/2015 | Kofoed | | |
| 2015/0152157 A1 | 6/2015 | Kofoed | | |
| 2016/0200791 A1 | 7/2016 | Sauerberg | | |

FOREIGN PATENT DOCUMENTS

| | | |
|---|---|---|
| WO | WO 1998/008871 | 3/1998 |
| WO | WO 1999/043705 | 9/1999 |
| WO | WO 1999/043706 | 9/1999 |
| WO | WO 1999/043707 | 9/1999 |

(Continued)

OTHER PUBLICATIONS

Manandhar, et al., “Glucagon-like Peptide-1 (GLP-1) Analogs: Recent Advances, New Possibilities, and Therapeutic Implications,” J Med Chem. 58(3): 1020-1037 (2015) (cited in IDS Filed Nov. 10, 2020) (Year: 2015).*

(Continued)

*Primary Examiner* — Satyanarayana R Gudibande
(74) *Attorney, Agent, or Firm* — McDonnell Boehnen Hulbert & Berghoff LLP

(57) ABSTRACT

The present disclosure pertains to novel Glucagon like Peptide-1 (GLP-1) (7-37) analogs having an amino acid sequence with Leu or Ile at the C-terminal. The new analogs are potent GLP-1 agonists with reduced adverse effect and improved duration of action. The present disclosure further relates to acylated derivatives of the new analogs which have further improved potency and duration of action and are suitable for oral administration. The analogs of present disclosure may be useful in treatment of diabetes and obesity.

19 Claims, 11 Drawing Sheets

Specification includes a Sequence Listing.

(56) References Cited

FOREIGN PATENT DOCUMENTS

| | | |
|---|---|---|
| WO | WO 1999/043708 | 9/1999 |
| WO | WO 2000/034331 | 6/2000 |
| WO | WO 2004/078777 | 9/2004 |
| WO | WO 2004/103390 | 12/2004 |
| WO | WO 2005/027978 | 3/2005 |
| WO | WO 2006/097537 | 9/2006 |
| WO | WO 2006/097538 | 9/2006 |
| WO | WO 2006/121860 | 11/2006 |
| WO | WO 2007/030519 | 3/2007 |
| WO | WO 2007/039140 | 4/2007 |
| WO | WO 2009/030771 | 3/2009 |
| WO | WO 2011/080103 | 7/2011 |
| WO | WO 2012/016419 | 2/2012 |
| WO | WO 2012/062803 | 5/2012 |
| WO | WO 2012/062804 | 5/2012 |
| WO | WO 2012/140117 | 10/2012 |
| WO | WO 2012/150503 | 11/2012 |
| WO | WO 2013/037690 | 3/2013 |
| WO | WO 2013/051938 | 4/2013 |
| WO | WO 2013/186240 | 12/2013 |
| WO | WO 2014/056872 | 4/2014 |
| WO | WO 2014/091316 | 6/2014 |
| WO | WO 2014/096145 | 6/2014 |
| WO | WO 2014/202727 | 12/2014 |
| WO | WO 2014/209886 | 12/2014 |
| WO | WO 2015/000942 | 1/2015 |
| WO | WO 2015/022400 | 2/2015 |
| WO | WO 2015/086686 | 6/2015 |
| WO | WO 2015/086731 | 6/2015 |
| WO | WO 2015/086733 | 6/2015 |
| WO | WO 2016/083499 | 6/2016 |
| WO | WO 2016/097108 | 6/2016 |
| WO | WO 2016/198544 | 12/2016 |
| WO | WO 2017/149070 | 9/2017 |
| WO | WO 2017/211922 | 12/2017 |
| WO | WO 2018/083335 | 5/2018 |
| WO | WO 2018/100135 | 6/2018 |
| WO | WO 2018/178796 | 10/2018 |

OTHER PUBLICATIONS

Manandhar et al., "Glucagon-like Peptide-1 (GLP-1) Analogs: Recent Advances, New Possibilities, and Therapeutic Implications," J Med Chem. 58(3): 1020-1037 (2015).

International Search Report for International Application No. PCT/IB2019/052835 dated Jul. 12, 2019 (pp. 1-5).

Written Opinion for International Application No. PCT/IB2019/052835 dated Jul. 12, 2019 (pp. 1-5).

International Preliminary Report on Patentability for International Application No. PCT/IB2019/052835 dated Oct. 65, 2020 (pp. 1-6).

* cited by examiner

2-Cl-Trt-Resin + 2-[2-(2-Fmoc-aminoethoxy)ethoxy]acetic acid

DIPEA

2-[2-(2-Fmoc-aminoethoxy)ethoxy]acetic acid-2-Cl-Trt-Resin

50% Piperidine in DMF

2-[2-(2-aminoethoxy)ethoxy]acetic acid-2-Cl-Trt-Resin

2-[2-(2-Fmoc-aminoethoxy)ethoxy]acetic acid, DIPC +HOBt

2-[2-[2-[[2-[2-(2-Fmoc-aminoethoxy)ethoxy]acetyl]amino]ethoxy]ethoxy]acetic acid-2-Cl-Trt-Resin 50% Piperidine in DMF 2-[2-[2-[[2-[2-(2-aminoethoxy)ethoxy]acetyl]amino]ethoxy]ethoxy]acetic acid-2-Cl-Trt-Resin Fmoc-Glu-OtBu +DIPC+HOBt 2-[2-[2-[[2-[2-[2-[[(4*S*)-4-Fmoc-amino-5-tert-butoxy-5-oxo-pentanoyl]amino]ethoxy]ethoxy]acetyl]amino]ethoxy] ethoxy]acetic acid-2-Cl-Trt-Resin 50% Piperidine in DMF 2-[2-[2-[[2-[2-[2-[[(4*S*)-4-amino-5-tert-butoxy-5-oxo-pentanoyl]amino]ethoxy]ethoxy]acetyl]amino]ethoxy]ethoxy] acetic acid-2-Cl-Trt-Resin Octadecanedioic acid mono tert-butyl ester +DIPC+HOBt

[2-[2-[2-[[2-[2-[2-[[(4*S*)-5-tert-butoxy-4-[(18-*tert*-butoxy-18-oxo-octadecanoyl)amino]-5-oxo-pentanoyl]amino]ethoxy]ethoxy]acetyl]amino]ethoxy]ethoxy]acetic acid]- 2-Cl-Trt-Resin Trifluoroethanol:DCM (1:1)

2-[2-[2-[[2-[2-[2-[[(4*S*)-5-tert-butoxy-4-[(18-*tert*-butoxy-18-oxo-octadecanoyl)amino]-5-oxo-pentanoyl]amino]ethoxy]ethoxy]acetyl]amino]ethoxy]ethoxy]acetic acid IBCF+NMM+HOSu tert-butyl 18-[[(1*S*)-1-*tert*-butoxycarbonyl-4-[2-[2-[2-[2-[2-[2-(2,5-dioxopyrrolidin-1-yl)oxy-2-oxo-ethoxy]ethoxy]ethylamino]-2-oxo-ethoxy]ethoxy]ethylamino]-4-oxo-butyl]amino]-18-oxo-octadecanoate

TFA

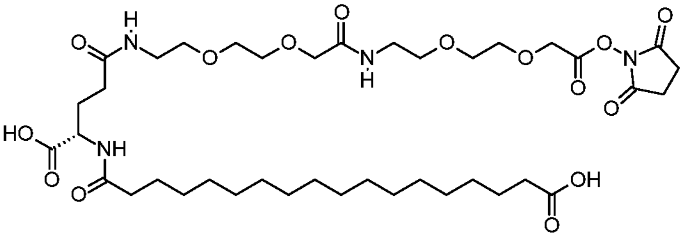

Moiety A-OSu

Figure 1A

2-Cl-Trt-Resin + 2-[2-(2-Fmoc-aminoethoxy)ethoxy]acetic acid

DIPEA

2-[2-(2-Fmoc-aminoethoxy)ethoxy]acetic acid-2-Cl-Trt-Resin

50% Piperidine in DMF

{2-(2-(2-amino-ethoxy)-ethoxy}-acetic acid-2-Cl-Trt-Resin

4-Nitropheylchloroformate + DIPEA

4-Fmoc-amino butylamine hydrochloride salt

DIPC +HOBt

2-[2-[2-(4-Fmoc-aminobutylcarbamoylamino)ethoxy]ethoxy]acetic acid-2-Cl-Trt-Resin 50% Piperidine in DMF Fmoc-Glu-OtBu +DIPC+HOBt 2-[2-[2-[4-[[(4S)-4-Fmoc-amino-5-tert-butoxy-5-oxo-pentanoyl]amino]butylcarbamoylamino]ethoxy]ethoxy]acetic acid-2-Cl-Trt-Resin 50% Piperidine in DMF Octadecanedioic acid mono *tert*-butyl ester +DIPC+HOBt 2-[2-[2-[4-[[(4*S*)-5-*tert*-butoxy-4-[(18-*tert*-butoxy-18-oxo-octadecanoyl)amino]-5-oxo-pentanoyl]amino]butylcarbamoylamino]ethoxy]ethoxy]acetic acid-2-Cl-Trt-Resin Trifluoroethanol:DCM (1:1)

2-[2-[2-[4-[[(4*S*)-5-tert-butoxy-4-[(18-*tert*-butoxy-18-oxo-octadecanoyl)amino]-5-oxo-pentanoyl]amino]butylcarbamoylamino]ethoxy]ethoxy]acetic acid DCC+HOSu

*tert*-butyl 18-[[(1*S*)-1-tert-butoxycarbonyl-4-[4-[2-[2-[2-(2,5-dioxopyrrolidin-1-yl)oxy-2-oxo-ethoxy]ethoxy]ethylcarbamoylamino]butylamino]-4-oxo-butyl]amino]-18-oxo-octadecanoate

TFA

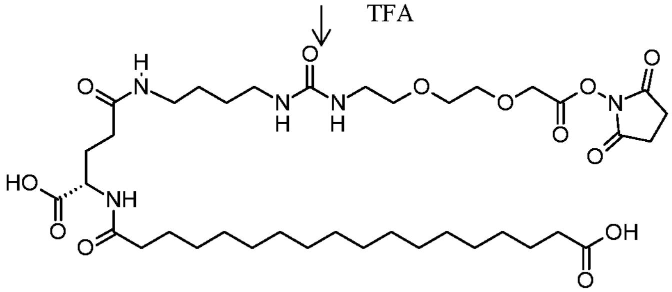

Moiety C-OSu

Figure 2

2-Cl-Trt-Resin + 2-[2-(2-Fmoc-aminoethoxy)ethoxy]acetic acid

DIPEA

2-[2-(2-Fmoc-aminoethoxy)ethoxy]acetic acid-2-Cl-Trt-Resin

50% Piperidine in DMF

2-[2-(2-aminoethoxy)ethoxy]acetic acid -2-Cl-Trt-Resin

Fmoc-Aib-OH
DIPC +HOBt

2-[2-[2-[(2-Fmoc-amino-2-methyl-propanoyl)amino]ethoxy]ethoxy]acetic acid-2-Cl-Trt-Resin 50% Piperidine
Fmoc-Glu-OtBu +DIPC+HOBt 2-[2-[2-[[2-[[(4*S*)-4-Fmoc-amino-5-*tert*-butoxy-5-oxo-pentanoyl]amino]-2-methyl-propanoyl] amino]ethoxy]ethoxy]acetic acid-2-Cl-Trt-Resin 50% Piperidine in DMF
Octadecanedioic acid mono *tert* butyl ester +DIPC+HOBt 2-[2-[2-[[2-[[(4*S*)-5-*tert*-butoxy-4-[(18-tert-butoxy-18-oxo-octadecanoyl)amino]-5-oxo-pentanoyl] amino]-2-methyl-propanoyl]amino]ethoxy]ethoxy]acetic acid-2-Cl-Trt-Resin Trifluoroethanol:DCM (1:1)

2-[2-[2-[[2-[[(4*S*)-5-tert-butoxy-4-[(18-*tert*-butoxy-18-oxo-octadecanoyl)amino]-5-oxo-pentanoyl] amino]-2-methyl-propanoyl]amino]ethoxy]ethoxy]acetic acid DCC+HOSu tert-butyl 18-[[(1S)-1-tert-butoxycarbonyl-4-[[2-[2-[2-[2-(2,5-dioxopyrrolidin-1-yl)oxy-2-oxo-ethoxy]ethoxy]ethylamino]-1,1-dimethyl-2-oxo-ethyl]amino]-4-oxo-butyl]amino]-18-oxo-octadecanoate

TFA

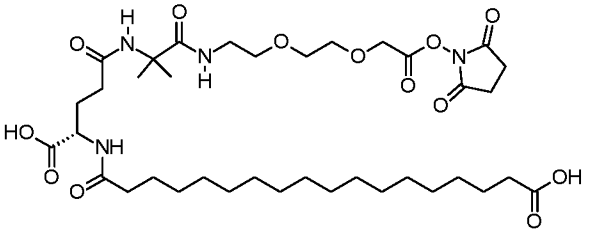

Moiety D-OSu

Figure 3

2-Cl-Trt-Resin + 2-[2-(2-Fmoc-aminoethoxy)ethoxy]acetic acid

DIPEA

2-[2-(2-Fmoc-aminoethoxy)ethoxy]acetic acid -2-Cl-Trt-Resin

50% Piperidine in DMF

2-[2-(2-aminoethoxy)ethoxy]acetic acid-2-Cl-Trt-Resin

4-Nitropheylchloroformate + DIPEA
1,3-Diaminopropane +HOBt
Fmoc-Glu-OtBu +DIPC+HOBt 2-[2-[2-[3-[[(4S)-4-Fmoc-amino-5-tert-butoxy-5-oxo-pentanoyl]amino]propylcarbamoylamino]ethoxy]ethoxy]acetic acid-2-Cl-Trt-Resin 50% Piperidine in DMF
Octadecanedioic acid mono *tert* butyl ester +DIPC+HOBt 2-[2-[2-[3-[[(4S)-5-tert-butoxy-4-[(18-tert-butoxy-18-oxo-octadecanoyl)amino]-5-oxo-pentanoyl]amino]propylcarbamoylamino]ethoxy]ethoxy]acetic acid-2-Cl-Trt-Resin Trifluoroethanol:DCM (1:1)

2-[2-[2-[3-[[(4S)-5-tert-butoxy-4-[(18-tert-butoxy-18-oxo-octadecanoyl)amino]-5-oxo-pentanoyl]amino]propylcarbamoylamino]ethoxy]ethoxy]acetic acid DCC+HOSu tert-butyl 18-[[(1S)-1-tert-butoxycarbonyl-4-[3-[2-[2-[2-(2,5-dioxopyrrolidin-1-yl)oxy-2-oxo-ethoxy]ethoxy]ethylcarbamoylamino]propylamino]-4-oxo-butyl]amino]-18-oxo-octadecanoate

TFA

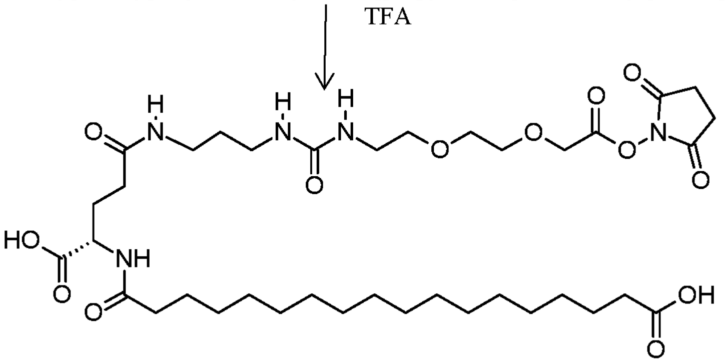

Moiety E-OSu

Figure 4

2-Cl-Trt-Resin + 2-[2-(2-Fmoc-aminoethoxy)ethoxy]acetic acid

DIPEA

2-[2-(2-Fmoc-aminoethoxy)ethoxy]acetic acid-2-Cl-Trt-Resin

50% Piperidine in DMF

2-[2-(2-aminoethoxy)ethoxy]acetic acid-2-Cl-Trt-Resin

4-Nitropheylchloroformate + DIPEA
4-Amino-Boc-piperidine
DIPEA +HOBt (2-[2-[2-(4-Boc-piperidylcarbamoylamino)ethoxy]ethoxy]acetic acid -2-Cl-Trt-Resin

TFA

2-[2-[2-(4-piperidylcarbamoylamino)ethoxy]ethoxy]acetic acid

Fmoc-OSu, TEA

2-[2-[2-(4-Fmoc-piperidylcarbamoylamino)ethoxy]ethoxy]acetic acid + 2-Cl-Trt-Resin

DIPEA

2-[2-[2-(4-Fmoc-piperidylcarbamoylamino)ethoxy]ethoxy]acetic acid-2-Cl-Trt-Resin 50% Piperidine in DMF
Fmoc-Glu-OtBu +DIPC+HOBt 2-[2-[2-[[1-[(4S)-4-amino-5-tert-butoxy-5-oxo-pentanoyl]-4-piperidyl]carbamoylamino]ethoxy]ethoxy]acetic acid-2-Cl-Trt-Resin 50% Piperidine in DMF
Octadecanedioic acid mono *tert* butyl ester +DIPC+HOBt 2-[2-[2-[[1-[(4S)-5-tert-butoxy-4-[(18-tert-butoxy-18-oxo-octadecanoyl)amino]-5-oxo-pentanoyl]-4-piperidyl]carbamoylamino]ethoxy]ethoxy]acetic acid-2-Cl-Trt-Resin Trifluoroethanol:DCM (1:1)

2-[2-[2-[[1-[(4S)-5-tert-butoxy-4-[(18-tert-butoxy-18-oxo-octadecanoyl)amino]-5-oxo-pentanoyl]-4-piperidyl]carbamoylamino]ethoxy]ethoxy]acetic acid DCC+HOSu tert-butyl 18-[[(1S)-1-tert-butoxycarbonyl-4-[4-[2-[2-[2-(2,5-dioxopyrrolidin-1-yl)oxy-2-oxo-ethoxy]ethoxy]ethylcarbamoylamino]-1-piperidyl]-4-oxo-butyl]amino]-18-oxo-octadecanoate

TFA

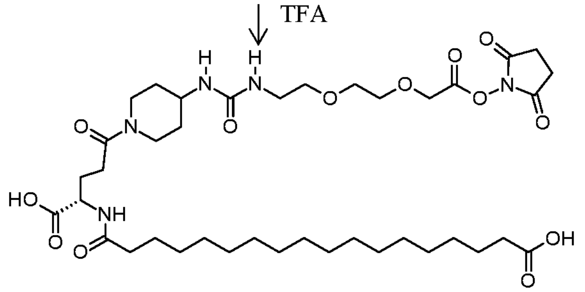

Moiety F-OSu

Figure 5

*p<0.05, p<0.01, *p<0.001 vs Diabetic Control; one way ANOVA followed by Dunnett's posttests

GLP-1 ANALOGUES

RELATED APPLICATIONS

This application is a continuation of U.S. application Ser. No. 16/376,190, filed Apr. 5, 2019, which claims the benefit of three Indian provisional applications having application nos. IN 201821013109 (filed on Apr. 05, 2018); IN 201821040468 (filed on Oct. 26, 2018) and IN 201821040474 (filed on Oct. 26, 2018), the disclosures of each of which are hereby incorporated by reference.

FIELD OF THE DISCLOSURE

The present disclosure relates to novel Glucagon like Peptide-1 (GLP-1) (7-38) analogs having an amino acid sequence with Leu or Ile at the C-terminal. The new analogs are potent GLP-1 agonists with reduced adverse effect and improved duration of action. The present disclosure further relates to acylated derivatives of the new analogs, which have further improved potency and duration of action and are suitable for oral administration. The analogs disclosed herein are acylated with protracting moieties, which increase the duration of activity of the compounds. The analogs disclosed herein may be useful in treatment of diabetes and obesity.

BACKGROUND OF THE DISCLOSURE

Glucagon-like peptide-1 (GLP-1) is a hormone that is mainly produced in enteroendocrine L cells of the gut and is secreted into the blood stream when food containing fat, protein hydrolysate and/or glucose enters the duodenum. GLP-1 is derived from the cell-specific post-translational processing of the preproglucagon gene. Initially, the peptide GLP-1(1-37) was identified from this processing, but it was the two N-terminally truncated products, GLP-1(7-37) (SEQ ID NO: 1) and GLP-1(7-36) amide, that were found to recognize the pancreatic receptor and which were determined to be the active species in vivo. GLP-1 has been found to stimulate insulin secretion, thereby causing glucose uptake by cells and decreased serum glucose levels. GLP-1 agonists are available for the treatment for Type 2 Diabetes Mellitus (T2DM) as favored drugs as they are devoid of hypoglycemia and with a positive benefit of weight loss. The endogenous substance, GLP-1(7-37) and GLP-1(7-36) amide, are cleaved by peptidases and thus have a very short half-life. Efforts were made to improve the performance by developing GLP-1 analogues with improved half-life. The first drug approved in 2005 was Exenatide with twice a day dosing at dose level 10 mcg and was found to show a significant improvement in HbA1c, a marker of glucose control. Further, Novo Nordisk developed Liraglutide (U.S. Pat. No. 6,268,343) (SEQ ID NO: 2) with once a day dosing of 1.8 mg, s.c./day and approved in 2010. Further research and development produced once a week products like, Albiglutide developed by GSK and Dulaglutide developed by Eli Lilly. Recently, Semaglutide (International Publication No. WO 2006/097537 A2), a GLP-1 analogue was approved by USFDA. Semaglutide (SEQ ID NO: 3) is marketed under the brand name Ozempic®. It is administered as a once-weekly subcutaneous injection.

Many attempts to make GLP-1 analogs having improved potency and duration of action are reported in literature. U.S. Pat. No. 7,291,594 B2 (the U.S. '594 patent) discloses GLP-1 (7-35) derivatives having added several residues of arginine and/or lysine to the C-terminus thereof to provide high bioavailability via mucous membranes. The U.S. '594 patent further discloses that these derivative can be conferred with resistance to dipeptidyl peptidase IV (DPP-IV) by substituting amino acid 8 in its GLP-1 amino acid sequence with Ser, or with resistance to trypsin by substituting amino acids 26 and 34 with Gln and Asn, respectively. U.S. Pat. No. 7,893,017 B2 (the U.S. '017 patent) discloses acylated GLP-1 analog wherein the GLP-1 analog is stabilized against DPP-IV by modification of at least one amino acid residue in positions 7 and 8 relative to the sequence GLP-1 (7-37) and wherein said acylation is a diacid attached directly to the C-terminal amino acid residue of said GLP-1 analog.

U.S. Pat. No. 8,951,959 B2 (the U.S. '959 patent) discloses a DPP-IV resistant GLP-1 (7-37) analogue having a non-proteogenic amino acid residue containing triflurom-ethyl group in position 8 relative to the sequence GLP-1, and is acylated with a moiety comprising two acidic groups to the lysine residue in position 26.

U.S. Pat. No. 7,084,243 B2 (the U.S. '243 patent) discloses GLP-1 (7-37) analogues having Val or Gly at position 8 relative to the sequence GLP-1 (7-37) as DPP-IV resistant peptides.

International Publication No. WO 2017/149070 A1(the WO '070) discloses GLP-1 analogues having a Trp at a position corresponding to position 8 of GLP-1 (7-37) and these Trp8 compounds were shown to be very stable against degradation by DPP-IV.

International Publication No. WO 2004/103390A2 (the WO '390) discloses that the modification at the $P'_1$ position (corresponding to 9 position in case of GLP-1 (7-37)) can produce GLP-1 analogues with greatly reduced susceptibility to enzyme-mediated (such as DPP-IV) cleavage relative to the native substrate, yet retain the biological activity of the native substrate. The WO '390 further discloses GLP-1 (7-37) analogues having an amino acid with tetrasubstituted Cβ carbon (such as tert-leucine) at position 9 provides GLP-analogues with resistant to degradation by DPP-IV.

International Publication No. WO 2015/086686 A2 (the WO '686 publication) discloses that incorporation of alpha-methyl-functionalized amino acids directly into the main chain of GLP-1 analogues has been determined to produce protease-resistant (includes DPP-IV resistant) peptides.

Various other DPP-IV resistant GLP-1 agonists are disclosed in patent publications such as International Publication Nos. WO 2007/030519 A2, WO 2004/078777 A2, WO 2007/039140 A1, WO 2014/209886 A1, WO 2012/016419 A1, WO 2017/211922 A2, WO 2016/198544 A1 and WO 2013/051938 A2.

Various patent applications disclose C-terminally extended GLP-1 analogues with increased stability and longer duration of action. For example, U.S. Pat. Nos. 7,482,321 B2, 9,498,534 B2 and 7,897,566 B2.

Various patent applications disclose acylated GLP-1 analogs wherein the GLP-1 analogues are attached to lipophilic substituent optionally via a linker to provide longer duration of action.

U.S. Pat. No. 8,603,972 B2 (the U.S. '972) discloses monoacylated derivatives of GLP-1 analogues wherein Lys residue at position 37 or 38 of GLP-1 analogue is acylated.

U.S. Pat. Nos. 8,648,041 B2, 9,758,560 B2, 9,006,178 B2, 9,266,940 B2, 9,708,383 B2 and United States Patent Application Publication Nos. US 2015/0152157 A1, US 2015/0133374 A1 disclose di-acylated derivatives of GLP-1 analogues.

United States Patent Application Publication No. US 2016/0200791 A1 discloses triacylated derivatives of GLP-1 analogues.

International Publication Nos. WO 2016/083499 A1, WO 2016/097108 A1 and WO 2014/202727 A1 disclose acylated GLP-1 analogues wherein the Lys residue of GLP-1 analogues is attached to two protracting moieties via a branched linker.

International Publication Nos. WO 2009/030771 A1 and WO 2018/083335 A1 disclose various acylating agents (side chain) which can be attached to Lys residue of GLP-1 analogues to provide longer duration of action.

International Publication No. WO 2013/186240 A2 discloses exendin-4 peptide analogues having Gly, Ser or functionalized Ser, e.g., Ser ($OCH_3$), D-Ser or functionalized D-Ser, e.g., D-Ser(OCH3), Aib, Ala, or D-Ala at position 2 of exendin-4 amino acid sequence.

Various other GLP-1 analogues are disclosed in patent applications such as International Publication Nos. WO 2005/027978 A2, WO 1998/008871 A1, WO 1999/043705 A1, WO 1999/043706 A1, WO 1999/043707 A1, WO 1999/043708 A1, WO 2000/034331 A2, WO 2009/030771 A1, WO 2011/080103 A1, WO 2012/140117 A1, WO 2012/062803 A1, WO 2012/062804 A1, WO 2013/037690 A1, WO 2014/202727 A1, WO 2015/000942 A1, WO 2015/022400 A1, WO 2016/083499 A1, WO 2016/097108 A1 and WO 2017/149070 A1.

Still, there is need to develop GLP-1 analogs which have optimum desired properties in terms of stability and duration of action.

SUMMARY OF THE DISCLOSURE

One aspect the present disclosure provides a polypeptide comprising the amino acid sequence:

H-X2-X3-X4-G-T-F-T-S-D-V-S-S-Y-L-X16-G-Q-A-A-X21-E-F-X24-A-W-L-V-R-G-R-G-X33-X34 wherein X2 is Ser, Ser(OMe), D-Ser, D-Ser(OMe), Ala or Aib;

X3 is absent or Gln;

X4 is Glu;

X16 is Glu;

X24 is Ile;

X33 is Leu, D-Leu, D-Ile or Ile;

X34 is absent and

X21 is Lys wherein the side chain amino (ε amino) group of Lys is acylated with a moiety:

{-Q-T-U-W-Y-Z wherein Q and T are absent;

U is absent or $—C(O)—CH_2—O—(CH_2)_2—O—(CH_2)_2—NH—\}$ wherein } is point of attachment with group W;

W is absent or selected from a group consisting of $—C(O)—CH_2—O—(CH_2)_2—O—(CH_2)_2—NH—]$, $—C(O)—NH—(CH_2)_{34}—NH—]$, $—C(O)—C(CH_3)_2—NH—]$ and

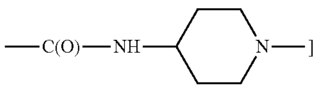

wherein ] is point of attachment with group Y;

Y is $—C(O)—(CH_2)_2—CH(COOH)NH—$, wherein — is point of attachment with the group Z;

Z is $—C(O)—(CH_2)_n—COOH$ or $—C(O)—(CH_2)_n—CH_3$ wherein n is an integer from 14 to 20.

The polypeptides of the present disclosure are potent GLP-1 agonists with fewer adverse effects. Further, the polypeptides of the present disclosure are stable and have long duration of action and are suitable for oral administration.

DESCRIPTION OF FIGURES

FIG. 1A illustrates the preparation of Moiety A-OSu (Intermediate 3).

FIG. 2 illustrates the preparation of Moiety C-OSu.

FIG. 3 illustrates the preparation of Moiety D-OSu.

FIG. 4 illustrates the preparation of Moiety E-OSu.

FIG. 5 illustrates the preparation of Moiety F-OSu.

ABBREVIATIONS

Figure 1B:
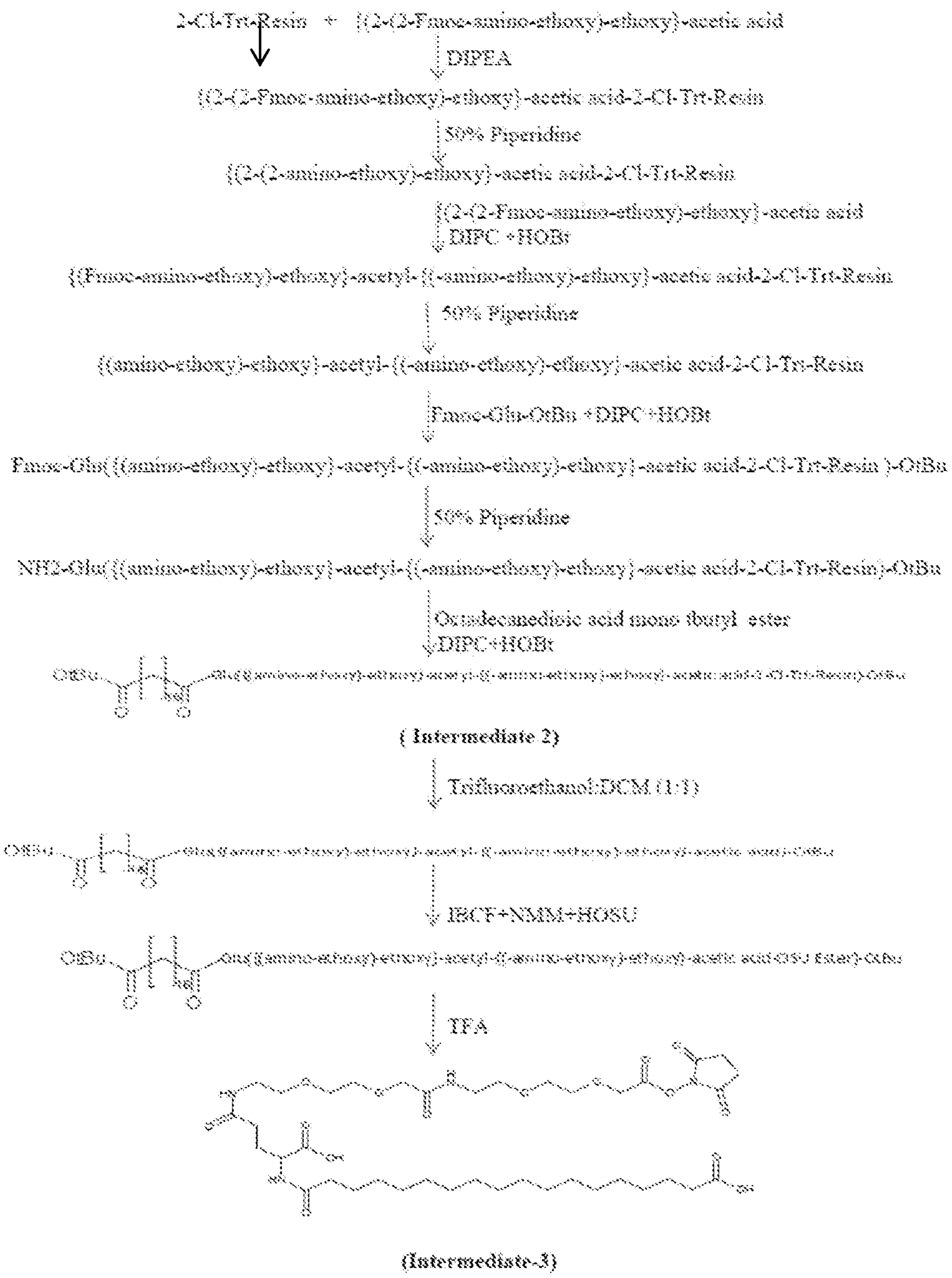
FIG. 1B illustrates the preparation of Moiety A-OSu (Intermediate 3).

Aib: 2-Aminoisobutyric acid
ADO: 8-Amino-3,6-dioxo-octanoic acid
OGTT: Oral glucose tolerance test
DIPEA: N,N'-Di-isopropylethylamine
HOBt: 1-Hydroxybenztriazole
DIPC: N,N'-Di-isopropylcarbodiimide
HOSu: N-Hydroxysuccinimide
IBCF: Isobutyl chloroformate
NMM: N-Methylmorpholine
THF: Tetrahydrofuran
DCM: Dichloromethane
DMAP: 4-Dimethylaminopyridine
DCC: Dicyclohexyl carbodiimide
DMAc: Dimethylacetamide

DESCRIPTION OF THE DISCLOSURE

The present disclosure provides a stable long acting GLP-1 analog, which does not require frequent subcutaneous dosing and is also suitable for oral administration. It was surprisingly found that the addition of an extra Leu at the C terminal of the sequence produced peptides with significantly improved potency and duration of action when compared to the parent peptide. The peptides with an extra Ile also showed similar effect of improved potency and duration of action when compared to the parent peptide. Additionally, the disclosure herein demonstrates moieties, which can be appended to peptides which are analogs of GLP-1(7-37) via acylation reaction to produce compounds with significantly improved potency and longer duration of action. The protracting moieties of the disclosed compounds have more stable bonds, which are less susceptible to cleavage by biological enzymes. Thus, the compounds disclosed herein are more stable and require less frequent administration adding to patient compliance. Accordingly, in some embodiments, the disclosure provides a polypeptide comprising the amino acid sequence:

```
                                   (SEQ ID NO: 4)
H-X2-X3-X4-G-T-F-T-S-D-V-S-S-Y-L-X16-G-Q-A-A-
X21-E-F-X24-A-W-L-V-R-G-R-G-X33-X34
```

wherein X2 is Ser, Ser(OMe), D-Ser, D-Ser(OMe), Ala or Aib;

X3 is absent or Gln;

X4 is Glu;

X16 is Glu;

X24 is Ile;

X33 is Leu, D-Leu, D-Ile or Ile;

X34 is absent and

X21 is Lys wherein the side chain amino (ε amino) group of Lys is acylated.

In some embodiments, X21 can be acylated with the protracting moieties reported in U.S. Pat. Nos. 6,268,343, 8,951,959 B2, 8,603,972 B2, 8,648,041 B2, 9,758,560 B2, 9,006,178 B2, 9,266,940 B2, 9,708,383 B2 and United States Patent Application Publication Nos. US 2015/0152157 A1 and US 2015/0133374 A1; International Publication Nos. WO 2009/030771 A1, WO 2006/097537 A2 and WO 2018/083335 A1.

In some embodiments, the X21 Lys is acylated at its side chain amino (ε amino) group with a moiety comprising a fatty acid group. The fatty acid group may be attached to X21 Lys via a linker. Accordingly, in some embodiments, the present disclosure provides a polypeptide comprising the amino acid sequence:

H-X2-X3-X4-G-T-F-T-S-D-V-S-S-Y-L-X16-G-Q-A-A-X21-E-F-X24-A-W-L-V-R-G-R-G-X33-X34 wherein X2 is Ser, Ser(OMe), D-Ser, D-Ser(OMe), Ala or Aib;

X3 is absent or Gln;

X4 is Glu;

X16 is Glu;

X24 is Ile;

X33 is Leu, D-Leu, D-Ile or Ile;

X34 is absent and

X21 is Lys wherein the side chain amino (ε amino) group of Lys is acylated with a moiety:

{-Q-T-U-W-Y-Z wherein Q and T are absent;

U is absent or $—C(O)—CH_2—O—(CH_2)_2—O—(CH_2)_2—NH—$} wherein } is point of attachment with group W;

W is absent or selected from a group consisting of $C(O)—CH_2—O—(CH_2)_2—O—(CH_2)_2—NH—$], $—C(O)—NH—(CH_2)_{34}—NH—$], $—C(O)—C(CH_3)_2—NH—$] and

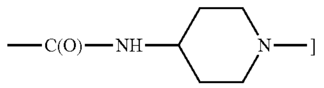

wherein ] is point of attachment with group Y;

Y is $—C(O)—(CH_2)_2—CH(COOH)NH—$, wherein — is point of attachment with the group Z;

Z is $—C(O)—(CH_2)_n—COOH$ or $—C(O)—(CH_2)_n—CH_3$ wherein n is an integer from 14 to 20.

In some embodiments, the amino acid at X2 is selected from Ser, Ser(OMe), D-Ser, D-Ser(OMe), Ala or Aib.

In some embodiments X2 is Aib.

In some embodiments, X3 is absent.

In some embodiments, X33 is Leu.

In some embodiments, X33 is Ile.

In some embodiments, X21 is Lys wherein the side chain amino (ε amino) group of Lys is acylated with a moiety:

{-Q-T-U-W-Y-Z, wherein W is selected from a group consisting of $C(O)—NH—(CH_2)_{3-4}—NH—$], $—C(O)—C(CH_3)_2—NH—$] and

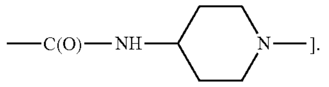

In some embodiments, X21 is Lys wherein the side chain amino (ε amino) group of Lys is acylated with a moiety:

{-Q-T-U-W-Y-Z, wherein U and W both are absent and Z is $—C(O)—(CH_2)_n—CH_3$ wherein n is an integer 14.

In some embodiments, X21 is Lys wherein the side chain amino (ε amino) group of Lys is acylated with a moiety:

{-Q-T-U-W-Y-Z, wherein W is $—C(O)—CH_2—O—(CH_2)_2—O—(CH_2)_2—NH$-1.

In some embodiments, X21 is Lys wherein the side chain amino (ε amino) group of Lys is acylated with a moiety:

{-Q-T-U-W-Y-Z, wherein W is $—C(O)—C(CH_3)_2—NH—$].

In some embodiments, X21 is Lys wherein the side chain amino (ε amino) group of Lys is acylated with a moiety:

{-Q-T-U-W-Y-Z, wherein W is $—C(O)—NH—(CH_2)_4—NH—$].

In some embodiments, X21 is Lys wherein the side chain amino (ε amino) group of Lys is acylated with a moiety:

{-Q-T-U-W-Y-Z, wherein W is $—C(O)—NH—(CH_2)_3—NH—$].

In some embodiments, X21 is Lys wherein the side chain amino (ε amino) group of Lys is acylated with a moiety:

{-Q-T-U-W-Y-Z, wherein W is

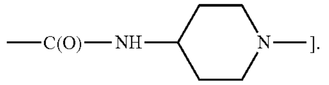

In some embodiments, X21 is Lys wherein the side chain amino (ε amino) group of Lys is acylated with a moiety:

{-Q-T-U-W-Y-Z, wherein Z is $—C(O)—(CH_2)_n—COOH$, wherein n is integer 16.

In some embodiments, X21 is Lys wherein the side chain amino (ε amino) group of Lys is acylated with a moiety:

{-Q-T-U-W-Y-Z, wherein Z is $—C(O)—(CH_2)_n—CH_3$ wherein n is an integer 14.

In some embodiments, X2 is Ala or Aib;

X3 is absent;

X33 is Leu;

U is absent;

W is absent;

Y is $—C(O)—(CH_2)_2—CH(COOH)NH—$, wherein — is point of attachment with the group Z;

Z is $—C(O)—(CH_2)n-CH_3$ wherein n is integer 14.

In some embodiments, the present disclosure provides a polypeptide comprising the amino acid sequence:

H-X2-X3-X4-G-T-F-T-S-D-V-S-S-Y-L-X16-G-Q-A-A-X21-E-F-X24-A-W-L-V-R-G-R-G-X33-X34 wherein X2 is Aib;

X3 is absent;

X4 is Glu;

X16 is Glu;

X24 is Ile;

X33 is Leu;

X34 is absent and

X21 is Lys wherein the side chain amino (ε amino) group of Lys is acylated with a moiety:

{-Q-T-U-W-Y-Z wherein Q and T are absent;

U is —C(O)—$CH_2$—O—$(CH_2)_2$—O—$(CH_2)_2$—NH—} wherein } is point of attachment with group W;

W is —C(O)—$CH_2$—O—$(CH_2)_2$—O—$(CH_2)_2$—NH—], wherein ] is point of attachment of group Y;

Y is —C(O)—$(CH_2)_2$—CH(COOH)NH—, wherein — is point of attachment with the group Z;

Z is —C(O)—$(CH_2)_n$—COOH wherein n is integer 16.

In some embodiments, the present disclosure provides a polypeptide comprising the amino acid sequence:

H-X2-X3-X4-G-T-F-T-S-D-V-S-S-Y-L-X16-G-Q-A-A-X21-E-F-X24-A-W-L-V-R-G-R-G-X33-X34 wherein X2 is Aib;

X3 is absent;

X4 is Glu;

X16 is Glu;

X24 is Ile;

X33 is Leu;

X34 is absent and

X21 is Lys wherein the side chain amino (ε amino) group of Lys is acylated with a moiety:

{-Q-T-U-W-Y-Z wherein Q and T are absent;

U is —C(O)—$CH_2$—O—$(CH_2)_2$—O—$(CH_2)_2$—NH—} wherein } is point of attachment with group W;

W is —C(O)—$C(CH_3)_2$—NH—] wherein ] is point of attachment with group Y;

Y is —C(O)—$(CH_2)_2$—CH(COOH)NH—, wherein — is point of attachment with the group Z;

Z is —C(O)—$(CH_2)_n$—COOH wherein n is integer 16.

In some embodiments, the present disclosure provides a polypeptide comprising the amino acid sequence:

H-X2-X3-X4-G-T-F-T-S-D-V-S-S-Y-L-X16-G-Q-A-A-X21-E-F-X24-A-W-L-V-R-G-R-G-X33-X34 wherein X2 is Aib;

X3 is absent;

X4 is Glu;

X16 is Glu;

X24 is Ile;

X33 is Leu;

X34 is absent and

X21 is Lys wherein the side chain amino (ε amino) group of Lys is acylated with a moiety:

{-Q-T-U-W-Y-Z wherein Q and T are absent;

U is —C(O)—$CH_2$—O—$(CH_2)_2$—O—$(CH_2)_2$—NH—} wherein } is point of attachment with group W;

W is —C(O)—NH—$(CH_2)_{3-4}$—NH—] wherein ] is point of attachment with group Y;

Y is —C(O)—$(CH_2)_2$—CH(COOH)NH—, wherein — is point of attachment with the group Z;

Z is —C(O)—$(CH_2)_n$—COOH wherein n is integer 16.

In some embodiments, X21 is Lys wherein the side chain amino (ε amino) group of Lys is acylated with a moiety:

{-Q-T-U-W-Y-Z, wherein W is —C(O)—NH—$(CH_2)_4$—NH—].

In some embodiments, X21 is Lys wherein the side chain amino (ε amino) group of Lys is acylated with a moiety:

{-Q-T-U-W-Y-Z, wherein W is —C(O)—NH—$(CH_2)_3$—NH—].

In some embodiments, the disclosure provides a polypeptide comprising the amino acid sequence:

H-X2-X3-X4-G-T-F-T-S-D-V-S-S-Y-L-X16-G-Q-A-A-X21-E-F-X24-A-W-L-V-R-G-R-G-X33-X34 wherein X2 is Aib;

X3 is absent;

X4 is Glu;

X16 is Glu;

X24 is Ile;

X33 is Leu;

X34 is absent and

X21 is Lys wherein the side chain amino (ε amino) group of Lys is acylated with a moiety:

{-Q-T-U-W-Y-Z, wherein Q and T are absent;

U is —C(O)—$CH_2$—O—$(CH_2)_2$—O—$(CH_2)_2$—NH—} wherein } is point of attachment with group W;

W is —C(O)—NH—$(CH_2)_4$—NH—], wherein ] is point of attachment of group Y;

Y is —C(O)—$(CH_2)_2$—CH(COOH)NH—, wherein — is point of attachment with the group Z;

Z is —C(O)—$(CH_2)_n$—COOH or —C(O)—$(CH_2)_n$—$CH_3$ wherein n is an integer from 14 to 20.

In some embodiments, X21 is Lys wherein the side chain amino (ε amino) group of Lys is acylated with a moiety:

{-Q-T-U-W-Y-Z, wherein Z is —C(O)—$(CH_2)_n$—COOH wherein n is integer 16.

In some embodiments, X21 is Lys wherein the side chain amino (ε amino) group of Lys is acylated with a moiety:

{-Q-T-U-W-Y-Z, wherein Z is —C(O)—$(CH_2)_n$—$CH_3$ wherein n is integer 14.

In some embodiments, the present disclosure provides a polypeptide comprising the amino acid sequence:

H-X2-X3-X4-G-T-F-T-S-D-V-S-S-Y-L-X16-G-Q-A-A-X21-E-F-X24-A-W-L-V-R-G-R-G-X33-X34 wherein X2 is Aib;

X3 is absent;

X4 is Glu;

X16 is Glu;

X24 is Ile;

X33 is Leu;

X34 is absent and

X21 is Lys wherein the side chain amino (ε amino) group of Lys is acylated with a moiety:

{-Q-T-U-W-Y-Z wherein Q and T are absent;

U is —C(O)—$CH_2$—O—$(CH_2)_2$—O—$(CH_2)_2$—NH—} wherein } is point of attachment with group W;

W is

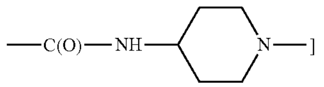

wherein ] is point of attachment with group Y;

Y is —C(O)—$(CH_2)_2$—CH(COOH)NH—, wherein — is point of attachment with the group Z; and Z is —C(O)—$(CH_2)$n-COOH wherein n is integer 16.

In some embodiments, the present disclosure provides a polypeptide comprising the amino acid sequence:

H-X2-X3-X4-G-T-F-T-S-D-V-S-S-Y-L-X16-G-Q-A-A-X21-E-F-X24-A-W-L-V-R-G-R-G-X33-X34 wherein X2 is Ser, Ser(OMe), D-Ser, D-Ser(OMe);

X3 is absent;

X4 is Glu;

X16 is Glu;

X24 is Ile;

X33 is Leu;

X34 is absent and

X21 is Lys wherein the side chain amino (ε amino) group of Lys is acylated with a moiety:

{-Q-T-U-W-Y-Z wherein Q and T are absent;

U is —C(O)—$CH_2$—O—$(CH_2)_2$—O—(CH2)$_2$—NH—} wherein } is point of attachment with group W;

W is —C(O)—$CH_2$—O—$(CH_2)_2$—O—$(CH_2)_2$—NH—, —C(O)—NH—$(CH_2)_{3-4}$—NH—], —C(O)—$C(CH_3)_2$—NH—], wherein ] is point of attachment with group Y;

Y is —C(O)—$(CH_2)_2$—CH(COOH)NH—, wherein — is point of attachment with the group Z; and Z is —C(O)—$(CH_2)_n$—COOH or —C(O)—$(CH_2)_n$—$CH_3$ wherein n is an integer from 14 to 20.

In some embodiments, X21 is Lys wherein the side chain amino (ε amino) group of Lys is acylated with a moiety:

{-Q-T-U-W-Y-Z, wherein W is —C(O)—NH—$(CH_2)_{3-4}$—NH—].

In some embodiments, X21 is Lys wherein the side chain amino (ε amino) group of Lys is acylated with a moiety:

{-Q-T-U-W-Y-Z, wherein W is —C(O)—$CH_2$—O—$(CH_2)_2$—O—$(CH_2)_2$—NH—;

In some embodiments, X21 is Lys wherein the side chain amino (ε amino) group of Lys is acylated with a moiety:

{-Q-T-U-W-Y-Z, wherein W is —C(O)—$C(CH_3)_2$—NH—]

In some embodiments, X21 is lipid modified Lys wherein the side chain amino (ε amino) group of Lys is acylated with a moiety

{-Q-T-U-W-Y-Z which is represented by the moieties provided in Table 1

TABLE 1

| Representative moieties for group {-Q-T-U-W-Y-Z | |
|---|---|
| Designation | Moiety |
| Moiety A | 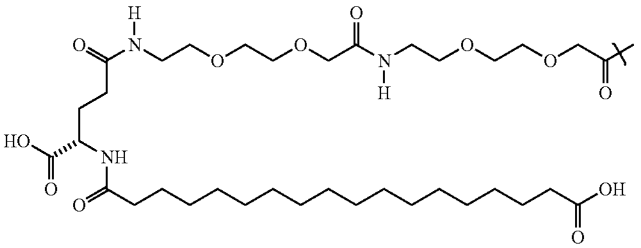 |
| Moiety B | 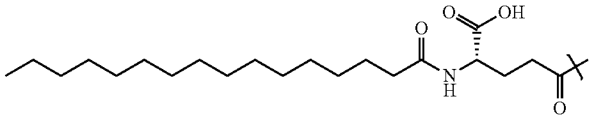 |
| Moiety C | 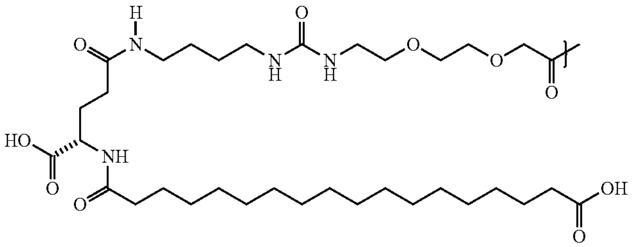 |
| Moiety D | 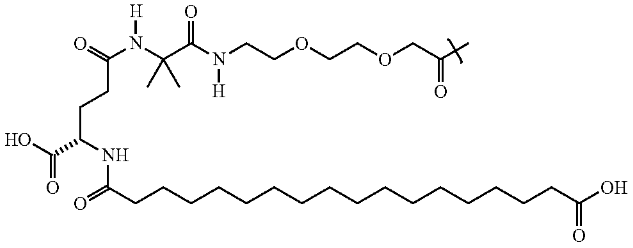 |

TABLE 1-continued
| Representative moieties for group {-Q-T-U-W-Y-Z | |
|---|---|
| Designation | Moiety |
| Moiety E | 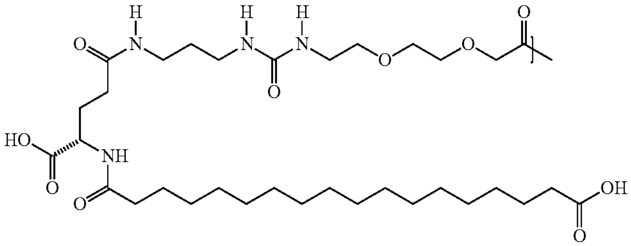 |
| Moiety F | 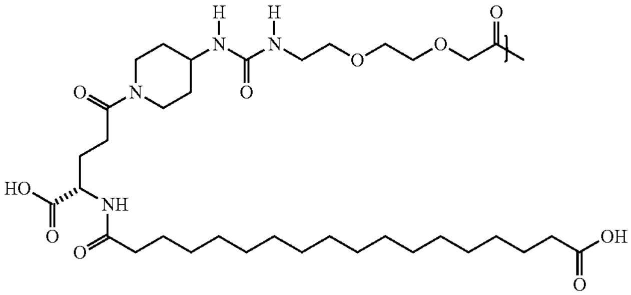 |
In another embodiment, the present disclosure provides a polypeptide according to any one of the preceding embodiments, which is selected from the peptides provided in Table 2:

TABLE 2
| Representative polypeptide compounds of present disclosure | | |
|---|---|---|
| Comp. # | Structure* | Seq ID |
| 1 | 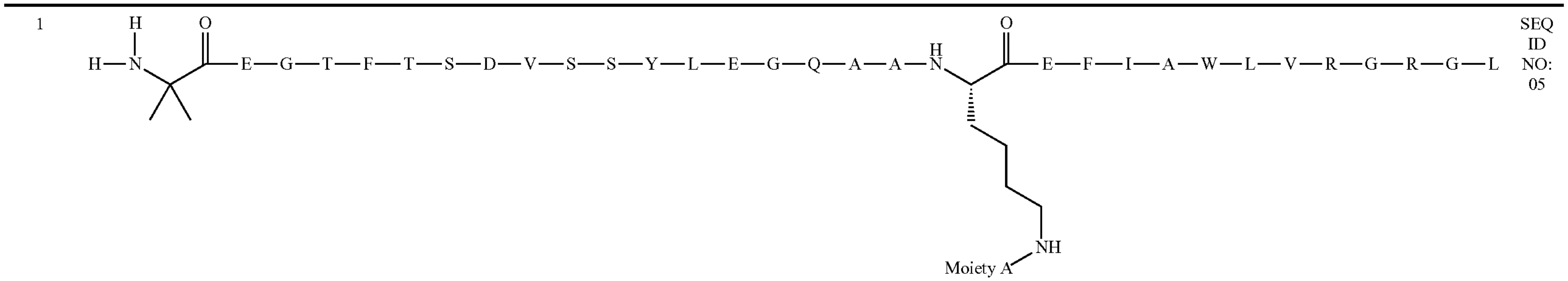 | SEQ ID NO: 05 |
| 2 | 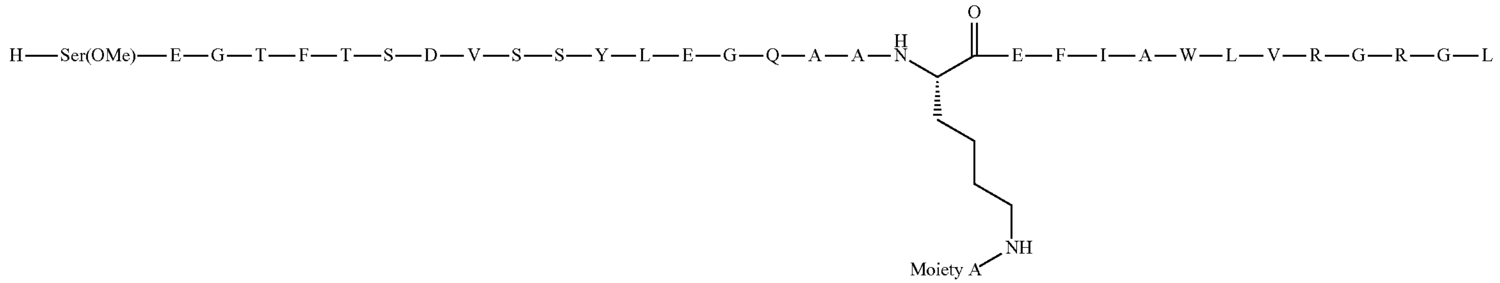 | SEQ ID NO:: 06 |
| 3 | 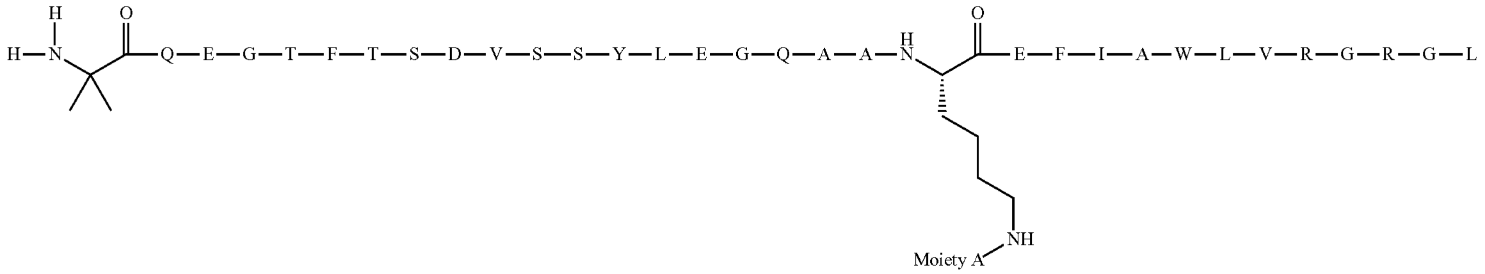 | SEQ ID NO: 07 |

TABLE 2-continued
Representative polypeptide compounds of present disclosure
| Comp. # | Structure* | Seq ID |
|---|---|---|
| 4 | 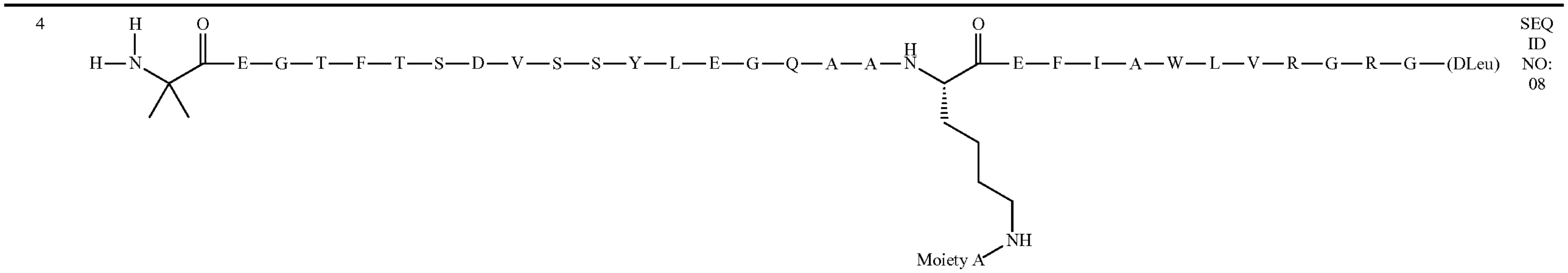 | SEQ ID NO: 08 |
| 5 | 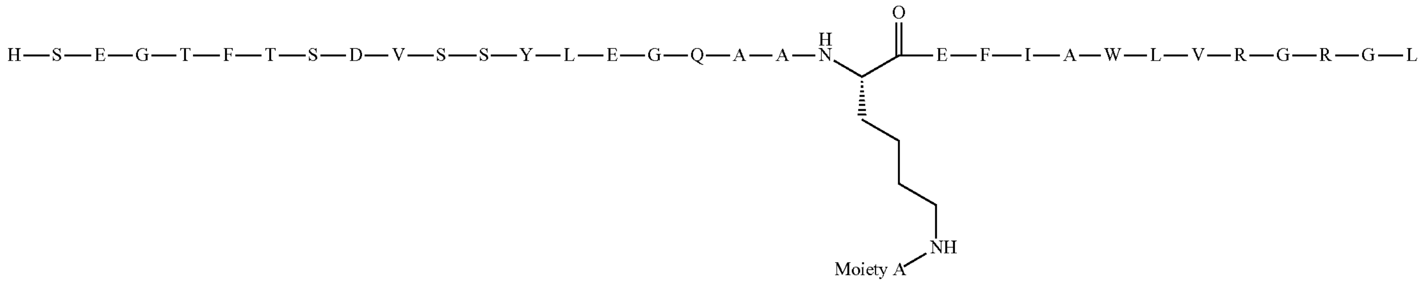 | SEQ ID NO:: 09 |
| 6 | 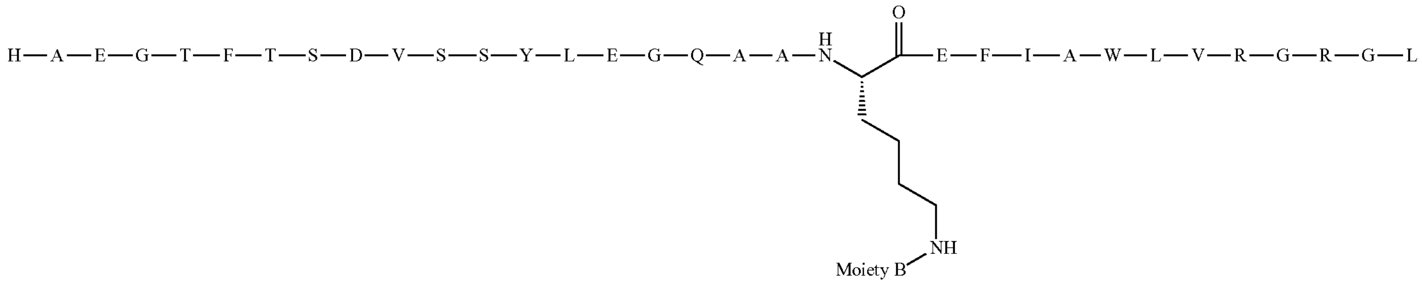 | SEQ ID NO: 10 |

TABLE 2-continued
| Representative polypeptide compounds of present disclosure | | |
|---|---|---|
| Comp. # | Structure* | Seq ID |
| 7 | 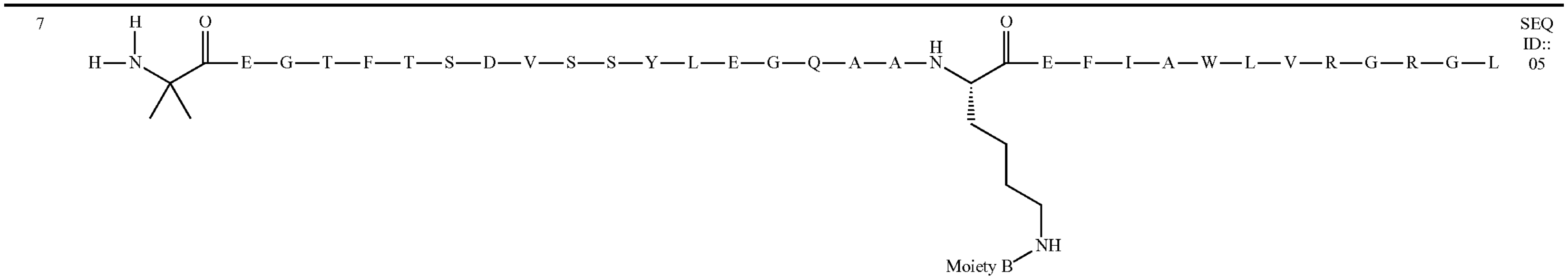 | SEQ ID:: 05 |
| 8 | 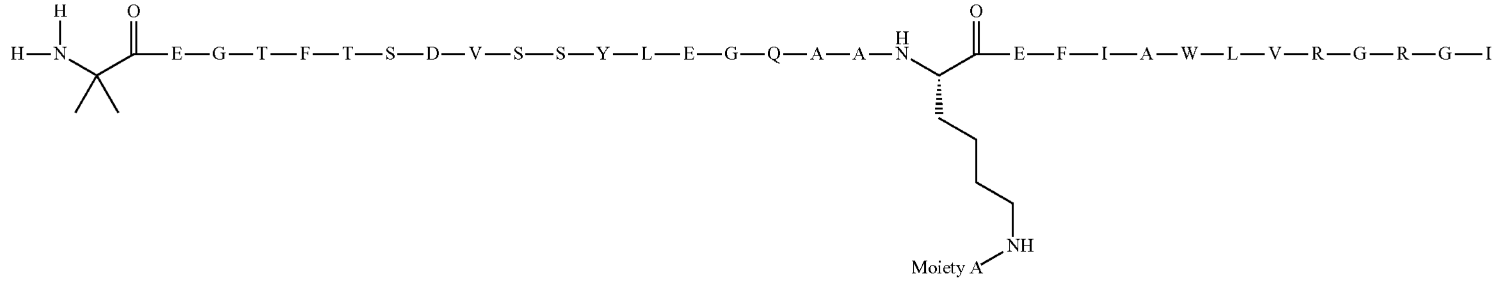 | SEQ ID NO: 11 |
| 9 | 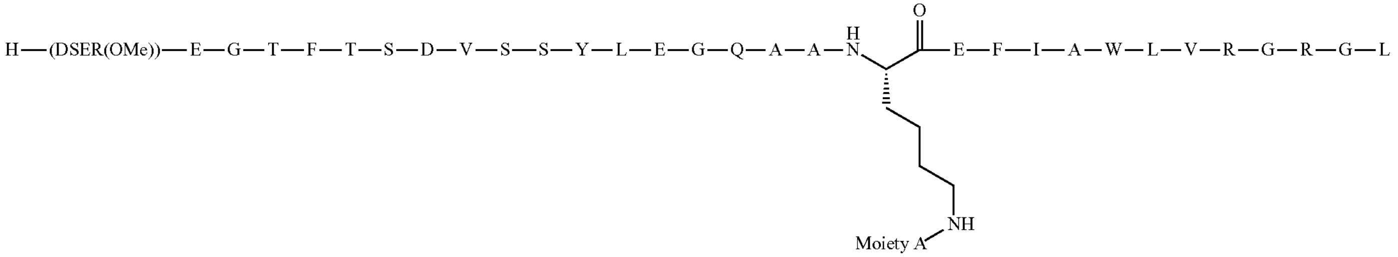 | SEQ ID NO: 12 |

TABLE 2-continued
| Representative polypeptide compounds of present disclosure | | |
|---|---|---|
| Comp. # | Structure* | Seq ID |
| 10 | 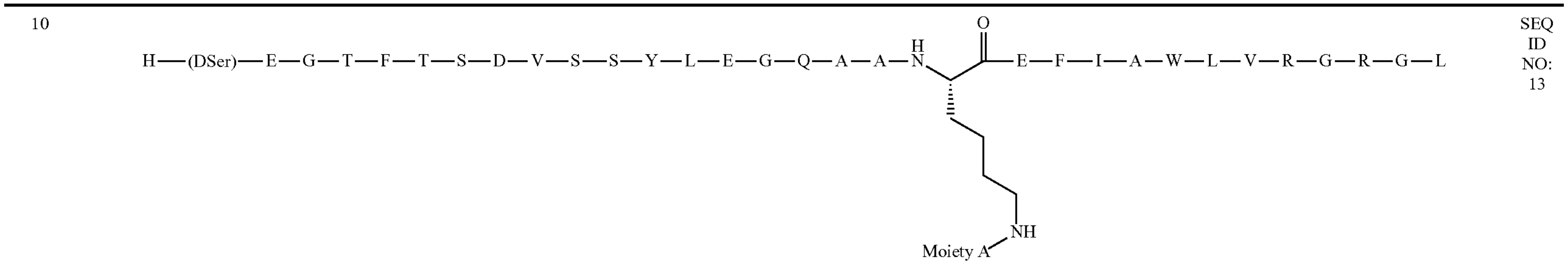 | SEQ ID NO: 13 |
| 11 | 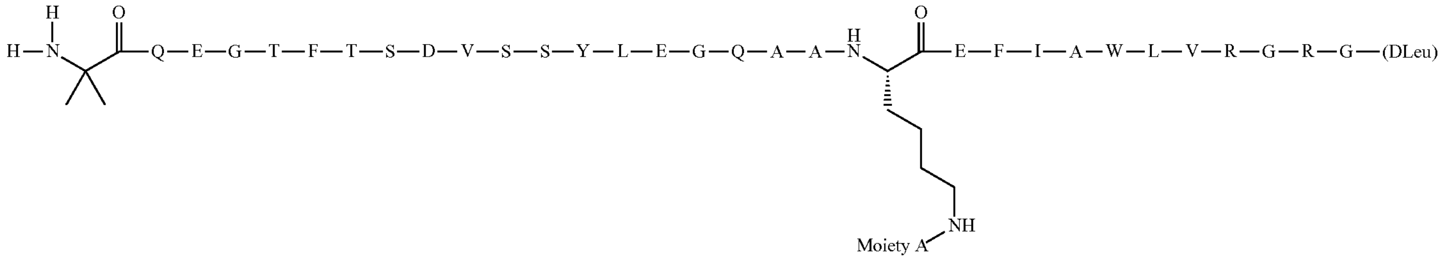 | SEQ ID NO: 14 |
| 12 | 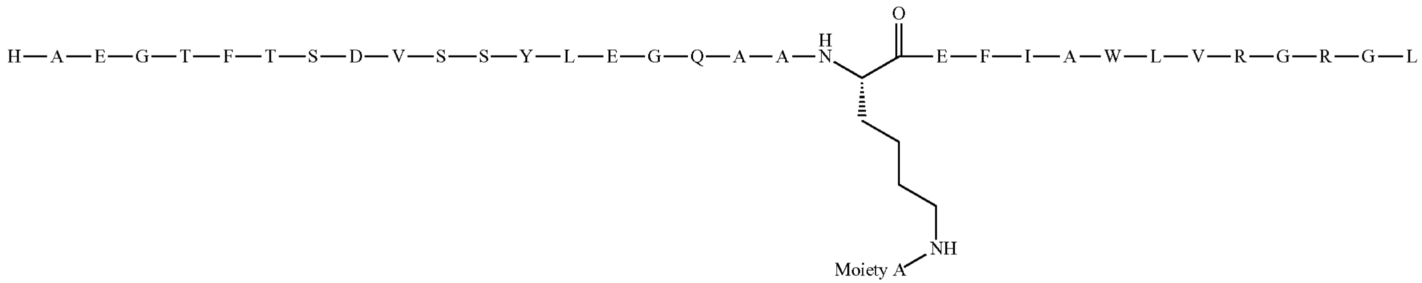 | SEQ ID NO: 10 |

TABLE 2-continued
| Representative polypeptide compounds of present disclosure | | |
|---|---|---|
| Comp. # | Structure* | Seq ID |
| 13 | 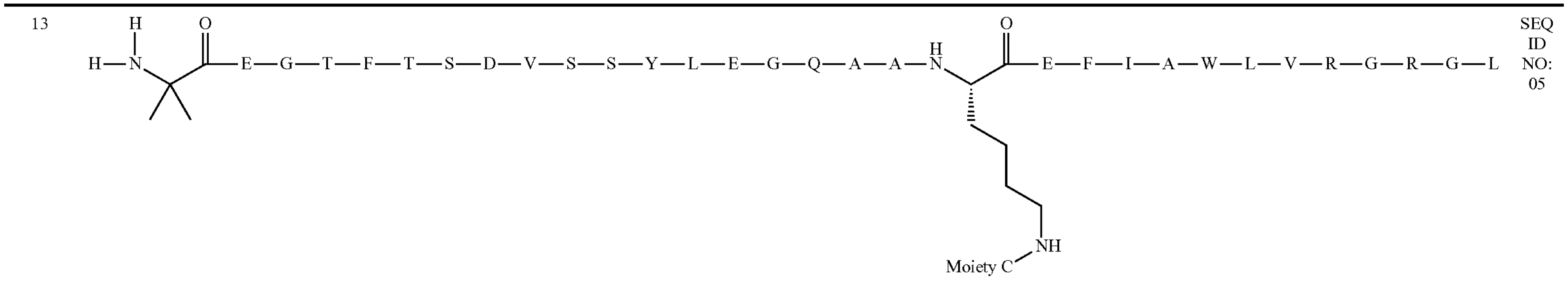 | SEQ ID NO: 05 |
| 14 | 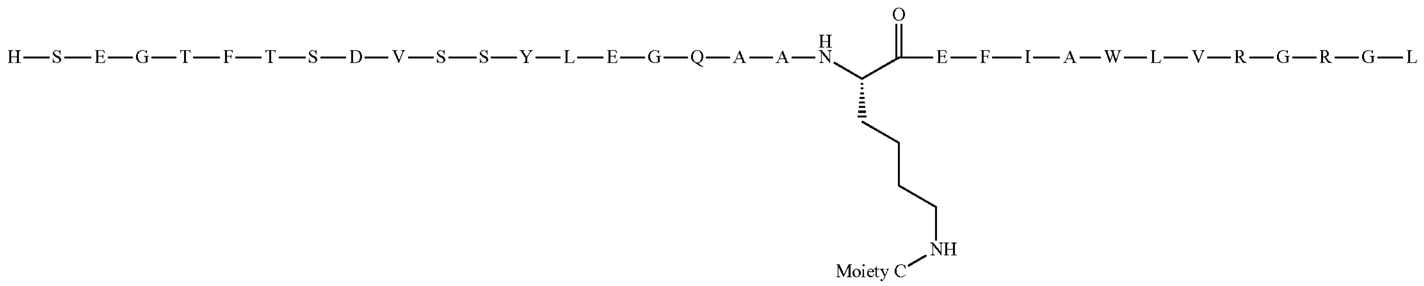 | SEQ ID NO:: 09 |
| 15 | 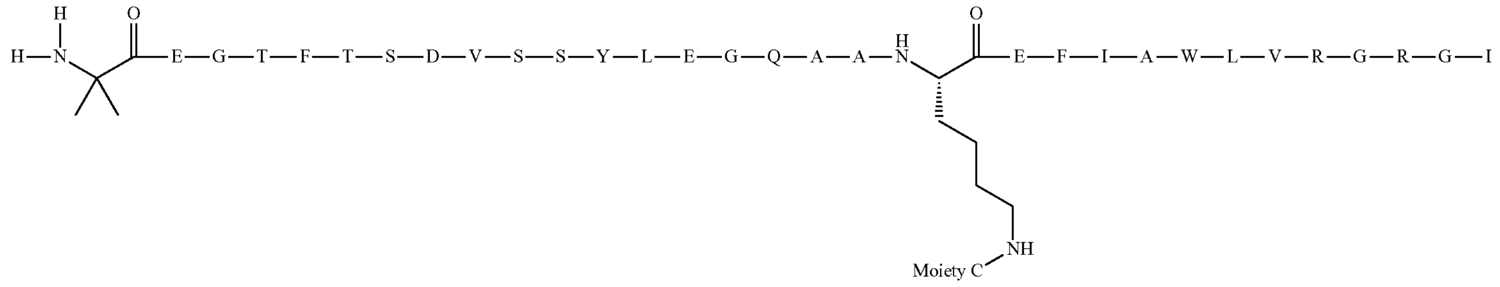 | SEQ ID NO: 11 |

TABLE 2-continued

| Representative polypeptide compounds of present disclosure | | |
|---|---|---|
| Comp. # | Structure* | Seq ID |
| 16 | 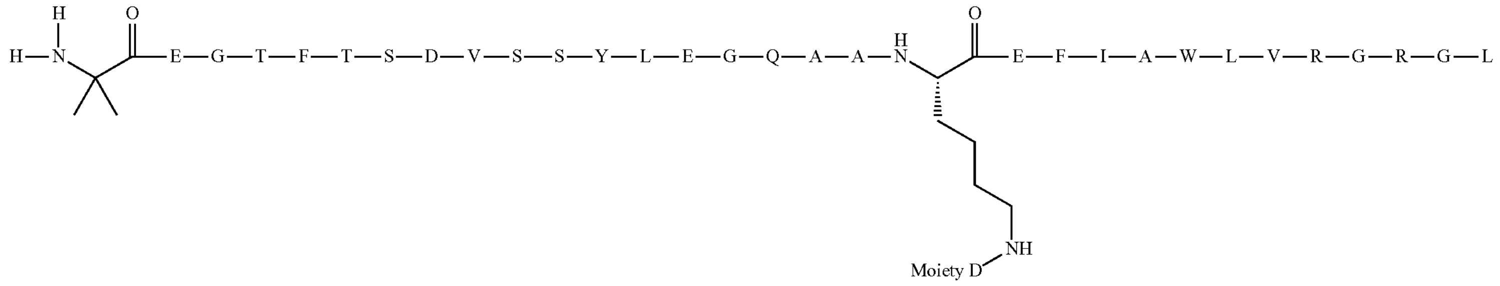 | SEQ ID NO: 05 |
| 17 | 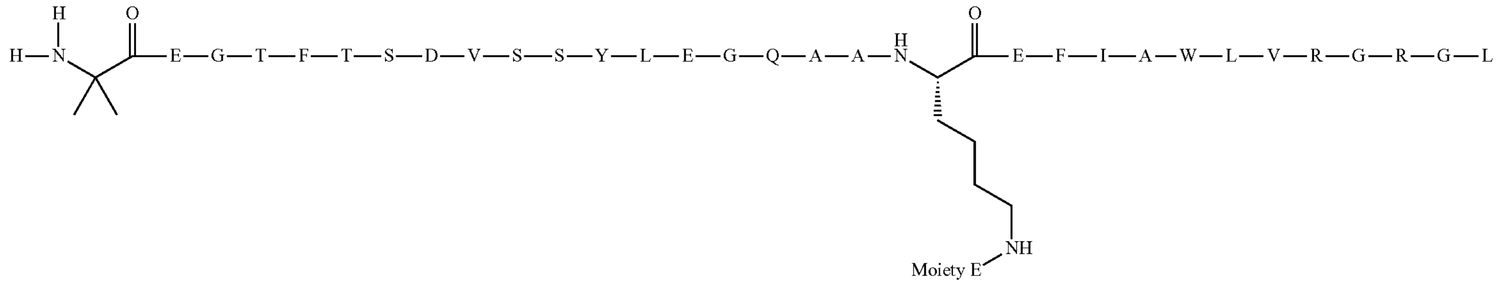 | SEQ ID NO: 05 |
| 18 | 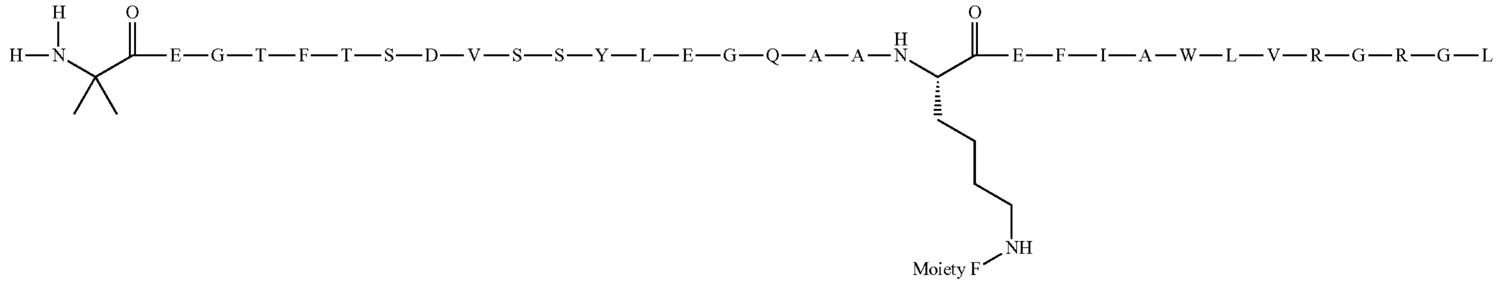 | SEQ ID NO: 05 |

*Unless stated otherwise, all the amino acids in the structures have L configuration at α position. D when used as a prefix to amino acid in the sequence denotes the D configuration of the amino acid. For example (DSer) denotes that Serine amino acid in the sequence has D-configuration.

Unless stated otherwise, the disclosure intends to cover both L and D isomers of the amino acids in the sequences.

Ser(OMe) as described herein in the disclosure is amino acid serine with its hydroxyl group methylated and has following structure.

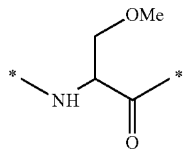

The polypeptide sequences mentioned in the disclosure are represented by the single letter code of the amino acids as approved by IUPAC.

Q, T, U, W, Y and Z as used herein to define the acylating moiety of the embodiments of the present disclosure are different than the single letter code of the amino acid used to denote the polypeptide sequence.

The polypeptides of the present disclosure surprisingly showed significant reduction in the blood glucose when subjected to an oral glucose tolerance test (OGTT) in SD rats. The percentage reduction of blood glucose in SD rats when challenged with oral glucose was significantly lower than the corresponding polypeptides which lacked the additional Leu or Ile at X33 position.

The present invention is further illustrated in detail with reference to the following examples. It is desired that the example be considered in all respect as illustrative and are not intended to limit the scope of the claimed invention.

EXAMPLES

General Methods of Preparation:

The polypeptide compound of the present disclosure can be prepared by methods described herein below. The process involves two steps, involving preparation of the parent linear peptide and subsequent attachment of fatty acid chain to the parent peptide.

The peptides described herein may be prepared by chemical synthesis using solid-phase techniques such as those described in G. Barany and R. B. Merrifield, "The Peptides: Analysis, Synthesis, Biology"; Volume 2—"Special Methods in Peptide Synthesis, Part A", pp. 3-284, E. Gross and J. Meienhofer, Eds., Academic Press, New York, 1980; and in J. M. Stewart and J. D. Young, "Solid-Phase Peptide Synthesis", 2nd Ed., Pierce Chemical Co., Rockford, Ill., 1984. The desired strategy is based on the Fmoc (9-Fluorenylmethyl-oxycarbonyl) group for temporary protection of the α-amino group, in combination with protecting groups such as tert-butyl (-tBu), tert-butyloxycarbonyl (-Boc), trityl (-Trt) groups for temporary protection of the amino acid side chains (see for example E. Atherton and R. C. Sheppard, "The Fluorenylmethoxycarbonyl Amino Protecting Group", in "The Peptides: Analysis, Synthesis, Biology"; Volume 9-"Special Methods in Peptide Synthesis, Part C", pp. 1-38, S. Undenfriend and J. Meienhofer, Eds., Academic Press, San Diego, 1987).

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively.

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The parent peptide can then be coupled to the fatty acid chain by coupling the activated fatty acid chain with the parent peptide. The fatty acid chain may be made by methods well known in organic chemistry. For example, the fatty acid chain can be made using solid phase synthetic methods which enables preparation of linear fatty acid chains.

The linear peptides synthesized were purified by preparative HPLC procedure as outlined below:

Preparative HPLC: WATERS 2555 Quaternary gradient module (Max Total Flow: 300 mL/min, Max Pressure: 3000 psi) or Shimadzu LC-8A (Max Total Flow: 150 mL: Max Pressure: 20 Mpa)

Column: C18, 10μ

Flow: 75 mL/min

Mobile Phase: For first purification

Mobile Phase A: pH 7.5 Phosphate buffer

Mobile Phase B: Acetonitrile

Gradient: 10 to 40% Mobile Phase-B in 300 min.

For second purification:

Mobile Phase A: 1% Acetic acid in water

Mobile Phase B: 1% Acetic acid in Acetonitrile:n-Propanol(50:50)

Gradient: 15 to 45% Mobile phase-B in 300 min

The final compounds of the present disclosure were purified by preparative HPLC procedure as outlined below:

Preparative HPLC: WATERS 2555 Quaternary gradient module (Max Total Flow: 300 mL/min, Max Pressure: 3000 psi) or Shimadzu LC-8A (Max Total Flow: 150 mL, Max Pressure: 20 Mpa)

Column: C18, 10μ

Flow: 75 mL/min

Mobile Phase:

| | For first purification | For second purification |
|---|---|---|
| Mobile Phase A | pH 7.5 Phosphate buffer | 1% Acetic acid in water |
| Mobile Phase B | Acetonitrile | 1% Acetic acid in Acetonitrile: n-Propanol (50:50) |
| Gradient | 10 to 40% Mobile Phase-B in 300 min | 15 to 45% Mobile Phase-B in 300 min |

The purity of the compounds of the present disclosure was analysed by RP-HPLC method as outlined below:

HPLC Method B1:

Column: YMC Pack-Ph (4.6 mm×150 mm 3μ)

Eluent: Mobile Phase A: 0.1% Trifluroacetic acid in Water

Mobile phase B: 0.1% Trifluroacetic acid in Acetonitrile
Flow rate: 1.5 mL/min
Detection: UV detection at 210 nm
Column Temperature: 50° C.
Run Time: 50 min.
Gradient:

| Time | Mobile Phase A % | Mobile Phase B % |
|---|---|---|
| 0.01 | 90 | 10 |
| 35.0 | 20 | 80 |
| 40.0 | 20 | 80 |
| 41.0 | 90 | 10 |
| 50.0 | 90 | 10 |

HPLC Method B2:
Column: YMC-Pack Pro C18 (4 mm×250 mm, 3μ)
Eluent: Mobile Phase A: Buffer: Acetonitrile (900:100)
Mobile phase B: Buffer: Acetonitrile (300:700
Buffer: Potassium dihydrogen orthophosphate in water, pH adjusted to 3.0±0.1 with orthophosphoric acid
Flow rate: 1.0 mL/min
Detection: UV detection at 210 nm
Column Temperature: 50° C.
Sample Tray temperature: 8° C.
Run Time: 38 min.

| Time | Mobile Phase A % | Mobile Phase B % |
|---|---|---|
| 0 | 100 | 0 |
| 5 | 100 | 0 |
| 30 | 0 | 100 |
| 32 | 0 | 100 |
| 32.1 | 100 | 0 |
| 38 | 100 | 0 |

HPLC Method B3:
Column: Waters X-Select CSH—C18 (150 mm×4.6 mm; 2.5μ)
Eluent: Mobile Phase A: Buffer: Acetonitrile (900:100)
Mobile phase B: Buffer: Acetonitrile (300:700
Buffer: Potassium dihydrogen orthophosphate in water, pH adjusted to 1.5±0.1 with orthophosphoric acid
Flow rate: 0.9 mL/min
Detection: UV detection at 210 nm
Column Temperature: 40° C.
Sample Tray temperature: 5° C.
Run Time: 100 min.

| Time | Mobile Phase A | Mobile Phase B |
|---|---|---|
| 0 | 50 | 50 |
| 40 | 43 | 57 |
| 55 | 43 | 57 |
| 90 | 0 | 100 |
| 91 | 50 | 50 |
| 100 | 50 | 50 |

The compounds of the present disclosure were analyzed by the LCMS as outlined below: Mass spectra were recorded on LCMS using Waters Acquity® QDa®, Waters Micromass Quattro Micro API or Thermo scientific LCQ Fleet™. The test solution was prepared by dissolving a suitable quantity of analyte in diluent with a final concentration from 1 μg/ml to 50 μg/ml depending on the ionization of analyte. The test solution was infused at a rate of about 10 μl to 50 μl per minute into LCMS for 1 min and mass spectra were recorded in Electro Spray Ionization (ESI) positive or negative mode and in an appropriate mass range.

Example 1: Preparation of Activated Fatty Acid Side Chains

1. Preparation of 18-[[(1S)-1-carboxy-4-[2-[2-[2-[2-[2-[2-(2,5-dioxopyrrolidin-1-yl)oxy-2-oxo-ethoxy]ethoxy]ethylamino]-2-oxo-ethoxy]ethoxy]ethylamino]-4-oxo-butyl]amino]-18-oxo-octadecanoic acid (Moiety A-OSu, Intermediate-3)

The activated fatty acid side chain, Moiety A-OSu was prepared by solid phase synthesis using 2-chlorotrityl chloride resin as schematically represented in FIG. 1A. 2-[2-(2-Fmoc-aminoethoxy)ethoxy]acetic acid (Intermediate-1) was attached to 2-chlorotrityl chloride resin in presence of N,N'-di-isopropylethylamine (DIPEA) which yielded 2-[2-(2-Fmoc-aminoethoxy)ethoxy] acetic acid-2-Cl-Trt-Resin. The intermediate-1 can be prepared by coupling of 2-[2-(2-amino ethoxy)-ethoxy] acetic acid with Fmoc N-hydroxysuccinimide ester. Alternatively, intermediate-1 is available commercially and can be procured as such. The Fmoc protecting group was removed by selective de-blocking of amino group of 2-[2-(2-Fmoc-aminoethoxy) ethoxy] acetic acid-2-Cl-Trt-Resin using piperidine and the free amino group was then coupled to 2-[2-(2-Fmoc-aminoethoxy) ethoxy]acetic acid using 1-hydroxybenztriazole (HOBt) and N,N'-di-isopropylcarbodiimide (DIPC) which yielded 2-[2-[2-[[2-[2-(2-Fmoc-amino ethoxy)ethoxy]acetyl]amino] ethoxy]ethoxy] acetic acid-2-Cl-Trt-Resin. The Fmoc group was then removed by selective de-blocking of amino group of 2-[2-[2-[[2-[2-(2-Fmoc-amino ethoxy)ethoxy]acetyl]amino]ethoxy]ethoxy] acetic acid-2-Cl-Trt-Resin using piperidine and the free amino group was then coupled to Fmoc-Glu-OtBu using HOBt and DIPC to obtain 2-[2-[2-[[2-[2-[2-[[(4S)-4-Fmoc-amino-5-tert-butoxy-5-oxo-pentanoyl] amino]ethoxy]ethoxy]acetyl]amino]ethoxy]ethoxy]acetic acid-2-Cl-Trt-Resin. The resultant 2-[2-[2-[[2-[2-[2-[[(4S)-4-Fmoc-amino-5-tert-butoxy-5-oxo-pentanoyl]amino] ethoxy]ethoxy]acetyl]amino]ethoxy]ethoxy]acetic acid-2-Cl-Trt-Resin was selectively deblocked using piperidine and then coupled with octadecanedioic acid mono tert-butyl ester to give intermediate-2 namely [2-[2-[2-[[2-[2-[2-[[(4S)-5-tert-butoxy-4-[(18-tert-butoxy-18-oxo-octadecanoyl)amino]-5-oxo-pentanoyl]amino]ethoxy]ethoxy] acetyl]amino] ethoxy]ethoxy] acetic acid]-2-Cl-Trt-Resin. The intermediate 2 was then cleaved from 2-Cl-Trt-Resin using trifluoroethanol:DCM (1:1). The resultant compound was then reacted with N-hydroxysuccinimide (HOSu) in presence of isobutyl chloroformate (IBCF) and N-methylmorpholine (NMM) followed by de-protection with trifluoroacetic acid to yield the title compound (Moiety A-OSu, intermediate-3). The whole process can also be depicted as schematically represented in FIG. 1B.

2. Preparation of N-palmitoyl-L-γ-glutamyl Succinimide Ester (Moiety B-OSu)

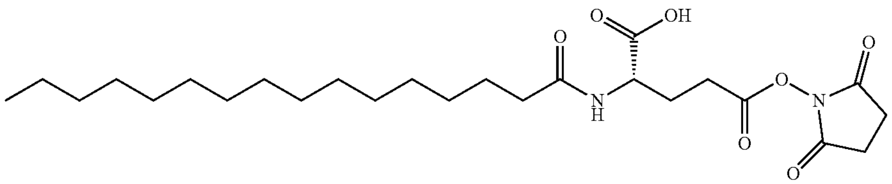

Moiety B-OSu

L-Glutamic acid alpha-tert-butyl ester (H-Glu-OtBu) was reacted with palmitic acid in presence of IBCF and NMM to yield $CH_3$—$(CH_2)_{14}$—C(O)-Glu-OtBu, which was then reacted with HOSu in the presence of IBCF and NMM to yield $CH_3$—$(CH_2)_{14}$—C(O)-Glu(OSu)-OtBu, which was then de-protected with trifluoroacetic acid to yield Moiety B-OSu.

3. Preparation of 18-[[(1S)-1-carboxy-4-[4-[2-[2-[2-(2,5-dioxopyrrolidin-1-yl)oxy-2-oxo-ethoxy]ethoxy]ethylcarbamoylamino]butylamino]-4-oxo-butyl]amino]-18-oxo-octadecanoic acid (Moiety C-OSu)

The activated fatty acid side chain, Moiety C-OSu was prepared using solid phase synthesis using 2-chlorotrityl chloride resin as schematically represented in FIG. 2. 2-[2-(2-Fmoc-aminoethoxy)ethoxy]acetic acid was attached to 2-chlorotrityl chloride resin in presence of DIPEA to yield 2-[2-(2-Fmoc-aminoethoxy)ethoxy]acetic acid-2-Cl-Trt-Resin. The Fmoc protecting group was removed by selective de-blocking of amino group using piperidine and the free amino group was then activated using p-nitrophenylchlroformate in THF and DIPEA followed by reaction with Fmoc-amino butylamine hydrochloride salt in THF: DMAc and DIPEA, which yielded 2-[2-[2-(4-Fmoc-aminobutylcarbamoylamino)ethoxy]ethoxy]acetic acid-2-Cl-Trt-Resin. The Fmoc group was removed by selective de-blocking using piperidine and the free amino group was then coupled to Fmoc-Glu-OtBu using of HOBt and DIPC, which yielded 2-[2-[2-[4-[[(4S)-4-Fmoc-amino-5-tert-butoxy-5-oxo-pentanoyl]amino] butylcarbamoylamino]ethoxy]ethoxy]acetic acid-2-Cl-Trt-Resin. The resultant 2-[2-[2-[4-[[(4S)-4-Fmoc-amino-5-tert-butoxy-5-oxo-pentanoyl]amino]-butylcarbamoylamino]ethoxy] ethoxy]acetic acid-2-Cl-Trt-Resin was selectively deblocked using piperidine and then coupled with octadecanedioic acid mono tert-butyl ester to give intermediate 2-[2-[2-[4-[[(4S)-5-tert-butoxy-4-[(18-tert-butoxy-18-oxo-octadecanoyl)amino]-5-oxo-pentanoyl] amino]butylcarbamoylamino]ethoxy]ethoxy]acetic acid-2-Cl-Trt-Resin. The intermediate was then cleaved from 2-Cl-Trt-Resin using trifluoroethanol:DCM (1:1) to obtain 2-[2-[2-[4-[[(4S)-5-tert-butoxy-4-[(18-tert-butoxy-18-oxo-octadecanoyl)amino]-5-oxo-pentanoyl] amino] butylcarbamoylamino]ethoxy]ethoxy] acetic acid (LCMS=m/z: 814.56 ($M+H^+$)). The resultant compound was then reacted with HOSu in presence of dicyclohexyl carbodiimide (DCC) to yield succinimide protected intermediate, which was de-protected with trifluoroacetic acid to yield the title compound (Moiety C-OSu).

4. Preparation of 18-[[(1S)-1-carboxy-4-[[2-[2-[2-[2-(2,5-dioxopyrrolidin-1-yl)oxy-2-oxo-ethoxy] ethoxy]ethylamino]dimethyl-2-oxo-ethyl]amino]-4-oxo-butyl]amino]-18-oxo-octadecanoic acid (Moiety D-OSu)

The fatty acid side chain was prepared using solid phase synthesis using 2-chlorotrityl chloride resin as schematically represented in FIG. 3. 2-[2-(2-Fmoc-aminoethoxy)ethoxy] acetic acid was attached to 2-chlorotrityl chloride resin in presence of DIPEA to yield 2-[2-(2-Fmoc-aminoethoxy) ethoxy]acetic acid-2-Cl-Trt-Resin. The Fmoc protecting group was removed by selective de-blocking of amino group using piperidine followed by coupling with Fmoc-Aib-OH in THF: DMAc using DIPC and HOBt which yielded 2-[2-[2-[(2-Fmoc-amino-2-methyl-propanoyl)amino] ethoxy]ethoxy]acetic acid-2-Cl-Trt-Resin. The Fmoc group was removed by selective de-blocking using piperidine and the free amino group was coupled with Fmoc-Glu-OtBu using HOBt and DIPC to yield 2-[2-[2-[[2-[[(4S)-4-Fmoc-amino-5-tert-butoxy-5-oxo-pentanoyl]amino]-2-methyl-prop amyl]amino] ethoxy]ethoxy]acetic acid-2-Cl-Trt-Resin. The Fmoc group of the resultant compound was selectively de-blocked using piperidine and the free amino group was then coupled with octadecanedioic acid mono tert butyl ester to give 2-[2-[2-[[2-[[(4S)-5-tert-butoxy-4-[(18amino]-5-oxo-pentanoyl]amino]-2-methyl-propanoyl]-amino ]ethoxy]ethoxy]acetic acid-2-Cl-Trt-Resin. The intermediate was then cleaved from 2-Cl-Trt-Resin using trifluoroethanol:DCM (1:1) to obtain 2-[2-[2-[[2-[[(4S)-5-tert-butoxy-4-[-tert-butoxy-18-oxo-octadecanoyl) (18-tert-butoxy-18-oxo-octadecanoyl)amino]-5-oxo-pentanoyl] amino]-2-methyl-propanoyl]amino]ethoxy]ethoxy]acetic acid (LCMS=m/z: 786.39 ($M+H^+$)). The resultant compound was then reacted with HOSu in presence of DCC to yield succinimide protected intermediate, which was de-protected with trifluoroacetic acid to yield the title compound (Moiety D-OSu).

5. Preparation of 18-[[(1S)-1-carboxy-4-[3-[2-[2-[2-(2,5-dioxopyrrolidin-1-yl)oxy-2-oxo-ethoxy]ethoxy] ethylcarbamoylamino]propylamino]-4-oxo-butyl] amino]oxo-octadecanoic acid (Moiety E-OSu)

The fatty acid side chain was prepared using solid phase synthesis using 2-chlorotrityl chloride resin as schematically represented in FIG. 4. 2-[2-(2-Fmoc-aminoethoxy)ethoxy] acetic acid was attached to 2-chlorotrityl chloride resin in presence of DIPEA to yield 2-[2-(2-Fmoc-aminoethoxy) ethoxy]acetic acid-2-Cl-Trt-Resin. The Fmoc protecting group was removed by selective de-blocking of amino group using piperidine and the free amino group was then activated using p-nitrophenylchloroformate in THF and DIPEA followed by reaction with 1,3-diaminopropane in THF: DMAc in presence of DIPEA using HOBt to form $NH_2$—$(CH_2)_3$—NH—C(O)-{(2-(2-amino-ethoxy)-ethoxy}-acetic acid-2-Cl-Trt-Resin. The free amino group was then coupled to Fmoc-Glu-OtBu using HOBt and DIPC, which yielded 2-[2-[2-[3-[[(4S)-4-Fmoc-amino-5-tert-butoxy-5-oxo-pentanoyl]amino] propylcarbamoylamino]ethoxy]ethoxy]acetic acid-2-Cl-Trt-Resin. The resultant 2-[2-[2-[3-[[(4S)-4-Fmoc-amino-5-tert-butoxy-5-oxo-pentanoyl]amino]propyl-carbamoylamino]ethoxy]-ethoxy ]acetic acid-2-Cl-Trt-Resin was selectively deblocked using piperidine and then coupled with octadecanedioic acid mono tert butyl ester to give 2-[2-[2-[3-[[(4S)-5-tert-butoxy-4-[(18-tert-butoxy-18-oxo-octadecanoyl)amino]-5-oxo-pentanoyl]amino]-propyl carbamoylamino]ethoxy]ethoxy]acetic acid-2-Cl-Trt-Resin. The intermediate was then cleaved from 2-Cl-Trt-Resin using trifluoroethanol:DCM (1:1) to obtain 2-[2-[2-[3-[[(4S)-5-tert-butoxy-4-[(18-tert-butoxy-18-oxo-octadecanoyl)amino]-5-oxo-pentanoyl]amino]-propylcarbamoylamino]ethoxy]ethoxy]acetic acid (LCMS=m/z: 801.41 ($M+H^+$)). The resultant compound was then reacted with HOSu in presence of dicyclohexyl carbodiimide (DCC) to yield succinimide protected intermediate, which was de-protected with trifluoroacetic acid to yield the title compound (Moiety E-OSu).

6. Preparation of 18-[[(1S)-1-carboxy-4-[4-[2-[2-[2-(2,5-dioxopyrrolidin-1-yl)oxy-2-oxo-ethoxy]ethoxy] ethylcarbamoylamino]-1-piperidyl]-4-oxo-butyl] amino]-18-oxo-octadecanoic acid (Moiety F-OSu)

The fatty acid side chain was prepared using solid phase synthesis using 2-chlorotrityl chloride resin as schematically represented in FIG. 5. 2-[2-(2-Fmoc-amino ethoxy)ethoxy] acetic acid was attached to 2-chlorotrityl chloride resin in presence of DIPEA to yield 2-[2-(2-Fmoc-aminoethoxy) ethoxy]acetic acid-2-Cl-Trt-Resin. The Fmoc protecting group was removed by selective de-blocking of amino group using piperidine and the free amino group was then activated using p-nitrophenylchloroformate in THF and DIPEA followed by reaction with 4-amino-Boc-piperidine in THF: DMAc in presence of DIPEA using HOBt which yielded (2-[2-[2-(4-Boc-piperidylcarbamoylamino) ethoxy]ethoxy] acetic acid-2-Cl-Trt-Resin. The resultant compound on cleavage using trifluoro acetic acid yielded 2-[2-[2-(4-piperidylcarbamoylamino)ethoxy]ethoxy]acetic acid which on further reaction with Fmoc-OSu in presence of triethylamine (TEA) yielded 2-[2-[2-(4-Fmoc-piperidylcarbamoylamino) ethoxy]ethoxy]acetic acid. The obtained compound was then further attached to 2-chlorotrityl chloride resin in presence of DIPEA to yield 2-[2-[2-(4-Fmoc-piperidylcarbamoylamino) ethoxy]ethoxy]acetic acid-2-Cl-Trt-Resin. The Fmoc group was removed by selective de-blocking using piperidine and the free amino group was then coupled with Fmoc-Glu-OtBu using HOBt and DIPC, which yielded 2-[2-[2-[[1-[(4S)-4-amino-5-tert-butoxy-5-oxo-pentanoyl]-4-piperidyl]carbamoylamino]ethoxy]ethoxy]acetic acid-2-Cl-Trt-Resin. The resultant compound was selectively deblocked using piperidine and was then coupled with octadecanedioic acid mono tert-butyl ester to give 2-[2-[2-[[1-[(4S)-5-tert-butoxy-4-[(18-tert-butoxy-18-oxo-octadecanoyl)amino]-5-oxo-pentanoyl]-4-piperidyl] carbamoylamino]ethoxy]ethoxy]acetic acid-2-Cl-Trt-Resin. Intermediate was then cleaved from 2-Cl-Trt-Resin using trifluoroethanol:DCM (1:1) to obtain 2-[2-[2-[[14(4S)-5-tert-butoxy-4-[(18-tert-butoxy-18-oxo-octadecanoyl) amino]-5-oxo-pentanoyl]-4-piperidyl]carbamoylamino] ethoxy]ethoxy]acetic acid (LCMS=m/z: 827.40 ($M+H^+$)). The resultant compound was then reacted with HOSu in presence of DCC to yield succinimide protected intermediate, which was de-protected using trifluoroacetic acid to yield the title compound, Moiety F-OSu.

Example 2: Synthesis of Compound 1

N-$\varepsilon^{26}$-[2-(2-[2-(2-[2-(2-[4-(17-Carboxyheptadecanoylamino)-4(S)carboxybutyrylamino]ethoxy) ethoxy]acetylamino)ethoxy]ethoxy)acetyl][(Aib$^8$, Arg$^{34}$, Leu$^{38}$ GLP-1(7-38) peptide Part A. Synthesis of the Parent Linear Peptide Aib$^8$, Arg$^{34}$, Leu$^{38}$ GLP-1(7-38)

The parent peptide was synthesized by solid-phase method. The starting resin used for synthesis was Wang resin. Fmoc protected Leucine was used for coupling with the Wang resin. The coupling was performed by using diisopropylcarbodiimide, N-hydroxybenzotriazole (DIC-HOBt) as coupling reagent in presence of 4-dimethylaminopyridine (DMAP) which yielded Fmoc-Leu-Wang Resin. Selective de-blocking of amino group of Fmoc-Leu-Wang Resin using piperidine followed by coupling with Fmoc-Gly-OH using HOBt and DIPC yielded Fmoc-Gly-Leu-Wang Resin. This completes one cycle. Acetic anhydride and diisopropylethyl amine/pyridine was used to terminate the uncoupled amino groups at every amino acid coupling.

The above 2 steps, i.e., selective deblocking of Fmoc-protection of amino acid attached to the resin and coupling of next amino acid residue in sequence with Fmoc-protected amino group were repeated for remaining 30 amino acid residues. The selective deblocking, i.e., deprotection of Fmoc group was done using piperidine and coupling with next Fmoc protected amino acid was done using HOBt/DIPC. The side chain of the Fmoc-protected amino acids were protected orthogonally, e.g., hydroxyl group of Serine, Tyrosine or Threonine were protected with tert-butyl(-tBu) group, amino and guanido group of Lysine and Arginine were protected with tert-butyloxycarbonyl (-Boc) and 2,2,4,6,7-pentamethyldihydrobenzofuran-5-sulfonyl (-Pbf) group respectively, the imidazole of histidine was protected with trityl (-Trt) and carboxylic acid groups of aspartic acid or glutamic acid were protected with tBu group. The above mentioned two steps, i.e., selective deblocking and then coupling with next Fmoc protected amino acid were performed to get Fmoc-His(Trt)-Aib-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln-Ala-Ala-Lys(Boc)-Glu (OtBu)-Phe-Ile-Ala-Trp-Leu-Val-Arg(Pbp-Gly- Arg(Pbf)-Gly-Leu-resin.

De-blocking of Fmoc-His(Trt)-Aib-Glu(OtBu)-Gly-Thr (tBu)-Phe-Thr(tBu)-Ser(tBu)-Asp(OtBu)-Val-Ser(tBu)-Ser (tBu)-Tyr(tBu)-Leu-Glu(OtBu)-Gly-Gln-Ala-Ala-Lys (Boc)-Glu(OtBu)-Phe-Ile-Ala-Trp-Leu-Val- Arg(Pbf)-Gly-Arg(Pbf)-Gly-Leu-Resin using piperidine followed by cleavage and de-protection using trifluoroacetic acid with ethane-1,2-dithiol resulted in crude H-His-Aib-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Arg-Gly-Arg-Gly-Leu-OH (Aib$^8$, Arg$^{34}$, Leu$^{38}$ GLP-1 (7-38) peptide) which was purified by HPLC.

Part B:

Grafting of activated fatty acid chain, Moiety A-OSu over purified (Linear Peptide) H-His-Aib-Glu-Gly-Thr-Phe-Thr-Ser-Asp-Val-Ser-Ser-Tyr-Leu-Glu-Gly-Gln-Ala-Ala-Lys- Glu-Phe-Ile-Ala-Trp-Leu- Val-Arg-Gly-Arg-Gly-Leu-OH obtained in Part A, in acetonitrile at pH about 10 resulted in crude title peptide which was purified by preparative HPLC. The characterization of the compounds is provided in Table 3.

Example 3: Preparation of Compound 2, 3, 5, 9, 10, and 12

The linear peptides of the compounds 2, 3, 5, 9, 10 and 12 were prepared by solid phase method as per the analogous process given for Example 1, Part A. Grafting of activated fatty acid chain, Moiety A-OSu by following the process of Example 1, Part B over the respective linear peptides afforded compound 2, 3, 5, 9, 10 and 12.

Example 4: Preparation of Compound 4 and 11

The linear peptides of the Compound 4 and 11 were prepared by solid phase method as per the analogous process given for Example 2, Part A except here Fmoc protected D-Leucine was first coupled with Wang resin and then sequentially other amino acids were coupled. Grafting of activated fatty acid chain, Moiety A-OSu over the respective linear peptide by following the process of Example 2, Part B afforded the Compound 4 and 11.

Example 5: Preparation of Compound 8

The linear peptide was prepared by solid phase method as per the analogous process given for Example 2, Part A except here Fmoc protected Isoleucine was first coupled with Wang resin and then sequentially other amino acids were coupled. The grafting of activated fatty acid chain, Moiety A-OSu over the linear peptide by following the process of Example 2, Part B afforded the Compound 8.

Example 6: Preparation of Compound 6

The linear peptide was prepared by solid phase method as per the analogous process given for Example 2, Part A. The grafting of activated fatty acid chain, Moiety B-OSu over the linear peptide by following analogous process of Example 2, Part B afforded the Compound 6.

Example 7: Preparation of Compound 7

The grafting of activated fatty acid chain, Moiety B-OSu over the linear peptide of the Example 2, Part A, by following analogous process of Example 2, Part B afforded the Compound 7.

Example 8: Preparation of Compound 13

The grafting of activated fatty acid chain, Moiety C-OSu over the linear peptide of the Example 1, Part A, by following analogous process of Example 1, Part B afforded the Compound 13.

Example 9: Preparation of Compound 14

The linear peptide was prepared by solid phase method as per the analogous process given for Example 2, Part A. The grafting of activated fatty acid chain, Moiety C-OSu over the linear peptide by following analogous process of Example 2, Part B afforded the Compound 14.

Example 10: Preparation of Compound 15

The linear peptide was prepared by solid phase method as per the analogous process given for Example 2, Part A starting with Fmoc protected Isoleucine was first coupled with Wang resin and then sequentially other amino acids were coupled. The grafting of activated fatty acid chain, Moiety C-OSu over the linear peptide by following analogous process of Example 2, Part B afforded the Compound 15.

Example 11: Preparation of Compound 16

The grafting of activated fatty acid chain, Moiety D-OSu over the linear peptide of the Example 2, Part A, by following analogous process of Example 2, Part B afforded the Compound 16.

Example 12: Preparation of Compound 17

The grafting of activated fatty acid chain, Moiety E-OSu over the linear peptide of the Example 2, Part A by following analogous process of Example 2, Part B afforded the Compound 17.

Example 13: Preparation of Compound 18

The grafting of activated fatty acid chain, Moiety F-OSu over the linear peptide of the Example 2, Part A, by following analogous process of Example 2, Part B afforded the Compound 18.

The characterization data of the synthesized compounds of the present disclosure are provided below in following Table 3.

TABLE 3

Characterization data of representative compounds of the present disclosure

| Comp. # | LCMS Data | HPLC Purity |
|---|---|---|
| 1 | m/z = 1057.52 ($MH_4^{4+}$), Calculated Mass = 4226.05 | 98.32% (Method B2), RT = 24.85 min. |
| 2 | m/z = 1061.74 ($MH_4^{4+}$), Calculated Mass = 4242.93 | 99.02% (Method B1), RT = 18.53 min. |
| 3 | m/z = 1087.65 $(M-4H)^{-4}$, Calculated Mass = 4354.63 | 98.12% (Method B1), RT = 18.48 min. |
| 4 | m/z =1055.68 $(M-4H)^{-4}$, Calculated Mass = 4226.75 | 98.97% (Method B1), RT = 18.32 min. |
| 5 | m/z = 1057.88 ($MH_4^{4+}$), Calculated Mass = 4227.49 | 96.75% (Method B1), RT = 17.09 min. |
| 6 | m/z = 967.26 ($MH_4^{4+}$), Calculated Mass: 3865.01 | 98.68% (Method B3), RT = 44.04 min. |
| 7 | m/z = 968.53 $(M-4H)^{-4}$, Calculated Mass = 3878.15 | 97.39% (Method B3), RT = 27.79 min. |
| 8 | m/z = 1057.72 ($MH_4^{4+}$), Calculated Mass = 4226.85 | 95.70% (Method B1), RT = 16.62 min. |
| 9 | m/z = 1061.67 ($MH_4^{4+}$), Calculated Mass = 4242.65 | 95.15% (Method B1), RT = 16.48 min. |
| 10 | m/z = 1058.18 ($MH_4^{4+}$), Calculated Mass = 4228.69 | 93.66% (Method B1), RT = 16.13 min. |
| 11 | m/z = 1056.95 ($MH_4^{4+}$), Calculated Mass: 4223.77 | 95.70% (Method B2), RT = 24.46 min |
| 12 | m/z = 1405.12 ($MH_3^{3+}$), Calculated Mass: 4212.34 | 97.51% (Method B1), RT = 19.06 min. |
| 13 | m/z = 1049.59 ($MH_4^{4+}$), Calculated Mass = 4194.33 | 96.01% (Method B2), RT = 25.16 min. |
| 14 | m/z = 1050.13 ($MH_4^{4+}$), Calculated Mass = 4196.49 | 92.06% (Method B2), RT = 24.55 min. |
| 15 | m/z = 1049.61 ($MH_4^{4+}$), Calculated Mass = 4194.41 | 94.41% (Method B2), RT = 24.82 min. |

TABLE 3-continued

Characterization data of representative compounds of the present disclosure

| Comp. # | LCMS Data | HPLC Purity |
|---|---|---|
| 16 | m/z = 1042.34 ($MH_4{}^{4+}$), Calculated Mass = 4165.32 | 94.56% (Method B2), RT = 25.26 min. |
| 17 | m/z = 1046.18 ($MH_4{}^{4+}$), Calculated Mass = 4180.72 | 94.33% (Method B2), RT = 25.17 min. |
| 18 | m/z = 1052.77 ($MH_4{}^{4+}$), Calculated Mass = 4207.08 | 93.12% (Method B2), RT = 24.92 min. |

Example 14: Oral Glucose Tolerance Test (OGTT) in Rats; Single Injection; 1 mg/kg Animals were divided into three groups a normal control group, a test group and a third semaglutide group, with 4 animals in each group. The animals were fasted for 12 hours before initiation of OGTT. To the test group animals, the Compound 1 was injected subcutaneously at 1 mg/kg dose. To the semaglutide group, a dose of 1 mg/kg was injected subcutaneously. After 22 hrs, 166 hrs and 334 hrs of subcutaneous injection of test drug or semaglutide, blood glucose was measured with blood glucose meter (time 0 measurements). All the animals were then given 2 g/kg of glucose solution orally. Blood glucose was measured at 20, 40, 60, 90 and 120 minutes following glucose challenge. Body weight and food intake was recorded. Blood glucose data was analyzed using Two way ANOVA followed by Bonferroni posttests using PRISM (Graph Pad version 5.03). Data of Blood glucose $AUC_{0\text{-}120\ min}$, was analyzed using t test.

Figure 6:
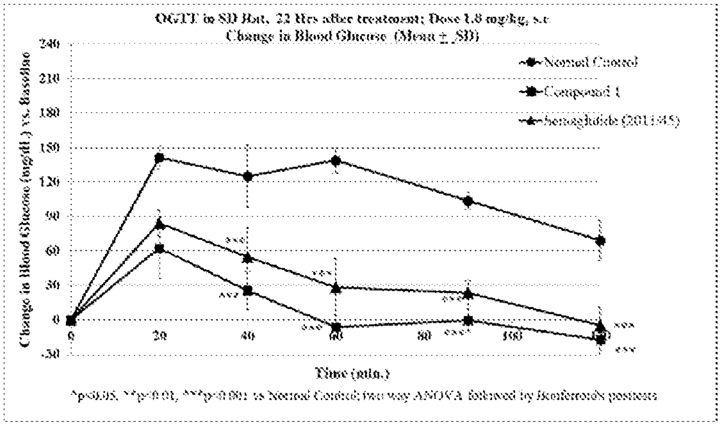
FIGS. 6A and 6B illustrate the results of an oral glucose tolerance test (OGTT) for Compound 1 in rats; single injection; 1 mg/kg glucose AUC 0-120 min (FIG. 6A=After 22 hrs, FIG. 6B=After 46 hrs).
Figure 6:
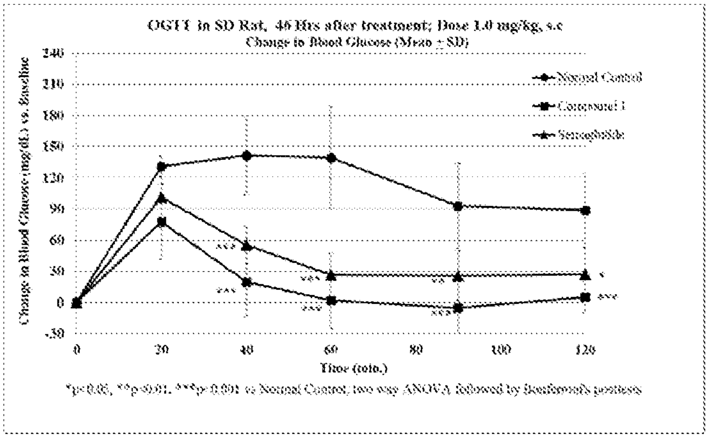

The polypeptides of the present disclosure have shown significant glucose lowering effect compared to the control group when studied in Oral Glucose Tolerance Test (OGTT) in rats. For example, FIG. 6 provides change in blood glucose level from time 0 to 120 min after 22 hrs and 46 hrs in the test group administered Compound 1 and the semaglutide treatment group. At 22 hours after single dosing, the Compound 1 showed statistically significant reduction in blood glucose level with $p<0.001$ vs normal control in ANOVA followed by Bonferroni's posttests. The glucose lowering effect of the Compound 1 was superior to the glucose lowering effect observed with semaglutide (see FIG. 6A). The superiority of glucose lowering effect of the Compound 1 was observed even after 46 hours of subcutaneous administration (FIG. 6B). Further, both the Compound 1 and semaglutide showed statistically significant reduction in food intake as compared to control when observed on day 2 as well as on day 4 (see Table 4 & 5). The reduced food intake shown by Compound 1 on day 4 was greater than semaglutide (see Table 5). In terms of body weight reduction, only the test compound showed significant reduction on body weight on day 4.

TABLE 4

Effect of treatment on food intake and body weight on Day 2

| | Food Consumption (g) (day 0 to day 2) | | Body Weight (g) (Day 2) | | |
|---|---|---|---|---|---|
| | Mean | SD | Mean | SD | % Change vs Baseline |
| Normal Control | 33.0 | 4.7 | 480.6 | 15.6 | 8.89 |
| Compound 1 | 2.63*** | 2.5 | 365.6 | 21.0 | −9.33 |
| Semaglutide | 5.03*** | 3.4 | 428.1 | 42.3 | −7.65 |

*p < 0.05,
**p < 0.01,
***p < 0.001 vs Normal Control; one way ANOVA followed by Bonferroni's posttests

TABLE 5

Effect of treatment on food intake and body weight on Day 4

| | Food Consumption (g) (day 0 to day 4) | | Body Weight (g) (Day 4) | | |
|---|---|---|---|---|---|
| | Mean | SD | Mean | SD | % Change vs Baseline |
| Normal Control | 90.5 | 5.6 | 491.3 | 16.9 | 2.1 |
| Compound 1 | 43.25***,## | 2.8 | 436.2* | 21.1 | −7.5 |
| Semaglutide | 55.73*** | 4.1 | 427.2 | 42.3 | −5.3 |

*p < 0.05,
**p < 0.01,
***p < 0.001 vs Normal Control; one way ANOVA followed by Bonferroni's posttests
#p < 0.05,
p < 0.01,
p < 0.001 vs Semaglutide; one way ANOVA followed by Bonferroni's posttests It was surprisingly found that compounds having X33 as Leu and Ile showed significant reduction of the blood glucose in the given studies whereas compounds with amino acids other than Leu and Ile had significantly less effect in lowering the blood glucose. The polypeptide of present disclosure has shown significant reduction in blood glucose when compared to the control group. Compounds having amino acids other than Leu or Ile at X33 positions were also tested. For example, Leu at 32nd position in Compound 1 (SEQ ID NO: 05) was replaced with Lys and Ser to obtain compounds Std-1 and Std-2, respectively. Std-1 and Std-2 showed only about 35 and 15% reduction in blood glucose $AUC_{0\text{-}120\ min}$ (Table 6).

TABLE 6

Percentage reduction in Blood Glucose $AUG_{0\text{-}120min}$ in OGTT test @ 1 mg/Kg dose after 24 hrs.

| Comp. # | % Glucose Reduction | Comp/std Semaglutide | Comp. # | % Glucose Reduction | Comp/std Liraglutide |
|---|---|---|---|---|---|
| Std-1 | 35.1 | 0.71 | 6 | 75.8 | 1.83 |
| Std-2 | 14.8 | 0.30 | 7 | 71.9 | 1.73 |
| Semaglutide | 49.3 | | Liraglutide | 41.5 | |

Similarly, the compound 6 which differs from liraglutide in having an additional Leu at 32nd position and the compound 7 which differs from liraglutide by having 2nd amino acid Ala replaced with Aib and having Leu as an additional 32nd amino acid, showed blood glucose lowering effect at 24 hrs which was significantly higher than liraglutide (Table 6).

Once it was determined that the Compound 1 was significantly better in terms of glucose reduction, food intake and body weight reduction, experiments were conducted to determine the duration of action of the compound of the present invention. The effect of the representative compounds of the present invention (Compound 1, 13 and 16) after 166 hrs (7 days) and 334 hrs (14 days) was studied and compared with that of semaglutide. The compounds were tested as per the method provided below:

Animals were divided into three groups—a normal control group, a test group and a third semaglutide group, with 4 animals in each group. The animals were fasted for 12 hours before initiation of OGTT. To the test group animals, Compound 1, Compound 13 and Compound 16 were injected subcutaneously at 1 mg/kg dose. To the semaglutide group, a dose of 1 mg/kg was injected subcutaneously. After 22 hrs, 166 hrs and 334 hrs of subcutaneous injection of test compound or semaglutide, blood glucose was measured with blood glucose meter (time 0 measurements). All the animals were then given 2 g/kg of glucose solution orally. Blood glucose was measured at 20, 40, 60, 90 and 120 minutes following glucose challenge. Body weight and food intake was recorded. Blood glucose data was analyzed using Two way ANOVA followed by Bonferroni posttests using PRISM (Graph Pad version 5.03). Data of Blood glucose $AUC_{0\text{-}120\ min}$, was analyzed using t test.

Table 7 provides the reduction in AUC of blood glucose for the representative compounds of present invention (Compound 1, 13 and 16) in comparison with the control group after 1 day, 7 days and 14 days of administration.

TABLE 7

Percentage reduction in Blood Glucose $AUC_{0\text{-}120min}$ in OGTT test @ 1 mg/Kg dose.

| Compound # | Time | Blood Glucose AUC (mg/dL*min) Mean | Change in AUC (mg/dL*min) |
|---|---|---|---|
| Semaglutide | 22 hr | 5458.0 | −63.4 |
| Exp. 1 | 168 hr | 12785.0 | −25.5 |
| | 336 hr | 16223.0 | −2.4 |
| Comp. 1 | 22 hr | 3173.0 | −78.7 |
| Exp. 1 | 168 hr | 5941.0 | −65.4 |
| | 336 hr | 11920.0 | −28.3 |
| Comp. 13 | 22 hr | 2795.0 | −81.2 |
| Exp. 1 | 168 hr | 6950.0 | −59.5 |
| | 336 hr | 11368.0 | −31.6 |
| Semaglutide | 22 hr | 4258 | −50 |
| Exp. 2 | 168 hr | 7410 | −26.6 |
| | 336 hr | 8023.0 | −5.5 |
| Comp. 16 | 22 hr | 1646 | −80.7 |
| Exp. 2 | 168 hr | 4283 | −57.6 |
| | 336 hr | 8295.0 | −2.3 |

Compounds 1 and 13 were studied and compared with semaglutide in one experiment (Exp. 1) and Compound 16 was studied and compared with semaglutide in a separate experiment (Exp. 2). After 168 hrs of injection, the Compound 1, 13 and 16 of present invention showed about 60% reduction in blood glucose AUC when compared to time zero blood glucose level. On the other hand, semaglutide showed just about 25% reduction in blood glucose level with respect to time zero blood glucose level.

Similar observations were made in quantity of food consumed and body weight change. As can be seen in the Table 8 below the animals administered with the representative compounds (Compound 1, 13 and 16) consumed significantly less food when compared to the animals administered with semaglutide. Compound 16 showed substantial lowering of body weight demonstrating potential utility for the treatment of obesity.

TABLE 8

Effect on food consumption and body weight in OGTT test @ 1 mg/Kg dose

| Compound # | Time | Food Consumption (g) Mean | Body Weight Change (%) Mean |
|---|---|---|---|
| Semaglutide | 48 h | 17.5 | −6.5 |
| Exp. 1 | 154 h | 86.3 | 4.5 |
| | 324 h | 107.9 | 11.8 |
| Comp. 1 | 48 h | 8.3 | −9.8 |
| Exp. 1 | 154 h | 69.6 | 5.2 |
| | 324 h | 99.4 | 9.3 |
| Comp. 13 | 48 h | 8.4 | −10.2 |
| Exp. 1 | 154 h | 62.3 | 4.5 |
| | 324 h | 82.44 | 8.2 |
| Semaglutide | 48 h | 19.3 | −8.7 |
| Exp. 2 | 154 h | 50.4 | 0.2 |
| | 324 h | 96.8 | 3.8 |
| Comp. 16 | 48 h | 5.9 | −10.7 |
| Exp. 2 | 154 h | 44.1.0 | −7.0 |
| | 324 h | 104.3 | −4.3 |

Example 15: Reduction of HbA1c in db/db Type 2 Diabetic Mice after Chronic Treatment This study was done in diabetic mouse model. The animals were divided into three treatment groups—a diabetic control group, a test group and a semaglutide treatment group. Compound 1 of the present disclosure was injected subcutaneously at 0.3 mg/kg dose once a day for 3 days (qd*3) followed by 0.1 mg/kg dose every alternate day for 7 doses (q2d*7) followed by 0.1 mg/kg dose once every four days for two dose cycles (q4d*2). The same dosage regimen was administered in semaglutide treatment group. Measurements of blood glucose levels and body weight were done daily. % HbA1c was measured on Day 0, day 7, day 14 and day 27 by column chromatography. Cumulative food intake was calculated on day 27. % HbA1C data was analyzed by two way ANOVA followed by Bonferroni's posttests using PRISM (Graph Pad version 5.03).

Figure 7:
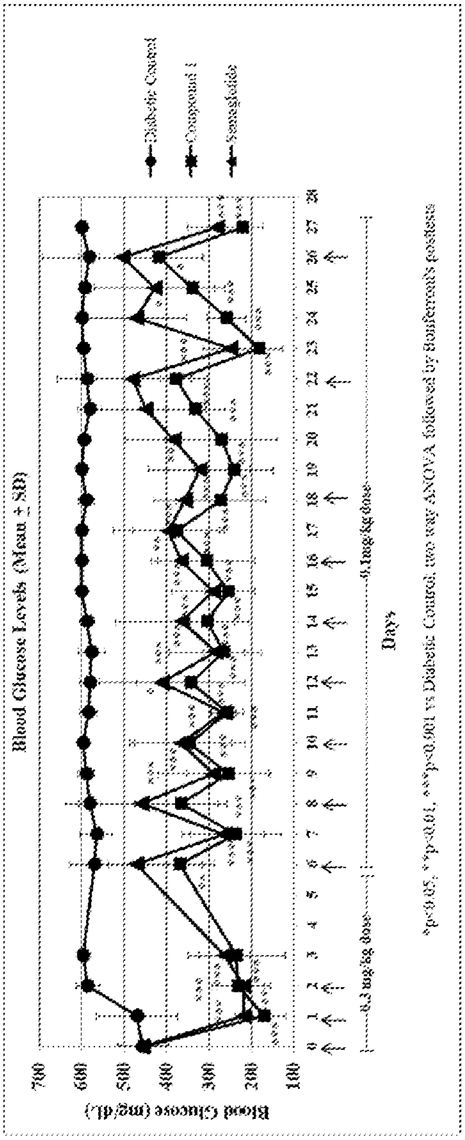
FIG. 7 illustrates the reduction in blood glucose levels in db/db type 2 diabetic mice after chronic treatment with Compound 1.
Figure 8:
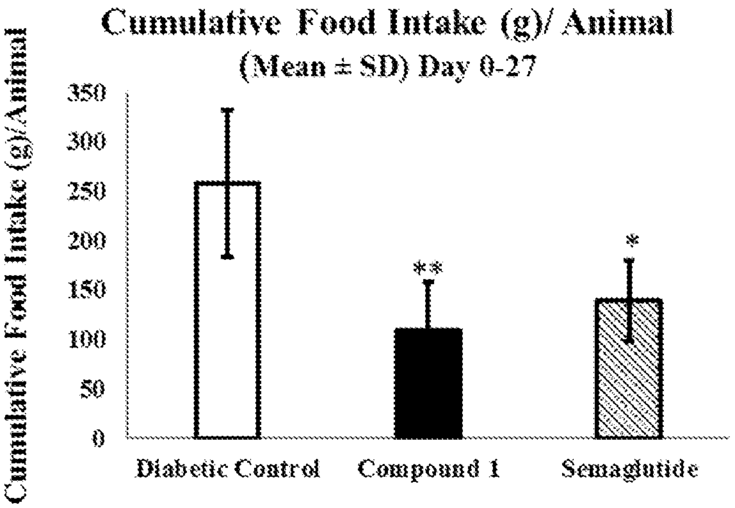
FIG. 8 illustrates the reduction in food intake in db/db mice following treatment with Compound 1.
Figure 9:
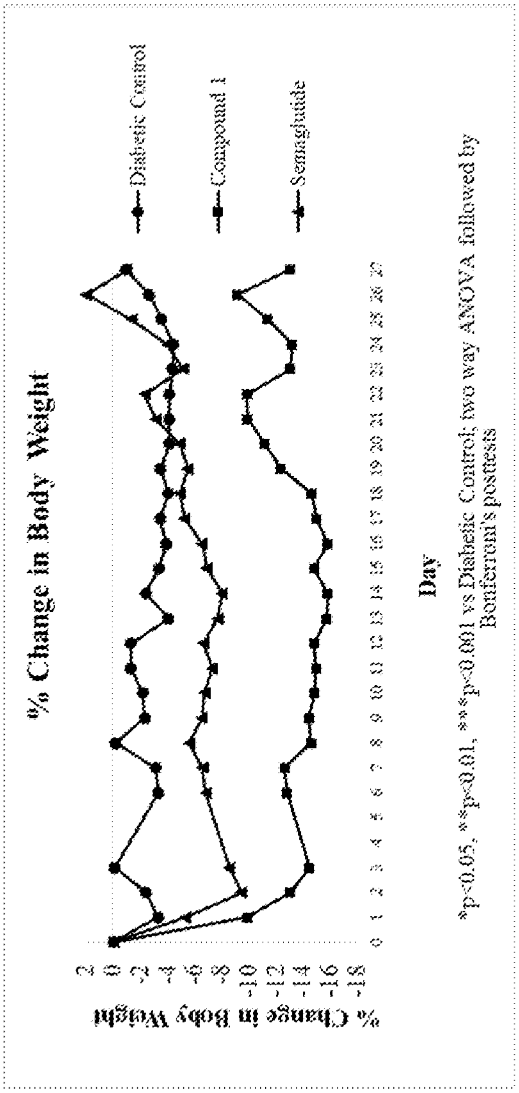
FIG. 9 illustrates the efficacy of Compound 1 in db/db mice in reduction of body weight.

The test group animals administered with the Compound 1 showed statistically significant reduction in blood glucose levels as compared to the diabetic control group (see FIG. 7), and the effect was superior to semaglutide treatment group in latter phase of the study. The test group animals administered with Compound 1 showed significant reduction in food intake as can be seen in the results provided in FIG. 8. FIG. 8 provides cumulative food intake from 0 to $27^{th}$ day by control and db/db mice treated with the test compound. Both the test compound and semaglutide showed a statistically significant reduction in food intake as compared to the diabetic control group. Further, the test compound showed a significantly lower food intake, as compared to semaglutide. In the same study, the Compound 1 has also shown significant reduction in body weight when compared to diabetic control group. FIG. 9 provides the result of % change in body weight for control and test group from day 0 to day 27. The test Compound 1 showed a significant reduction of −16% as compared to −8% as observed in semaglutide treatment group (see FIG. 09).

Figure 10:
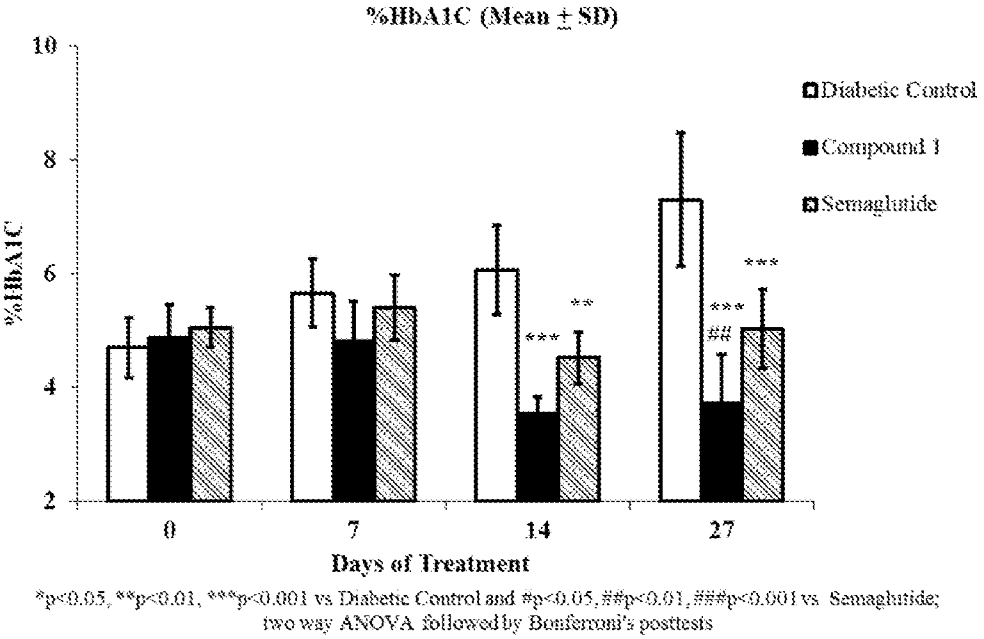
FIG. 10 illustrates the reduction in Hb1Ac in db/db mice following treatment with Compound 1.

In diabetes mellitus, higher amounts of HbA1c, indicating poorer control of blood glucose levels, have been associated with cardiovascular disease, nephropathy, neuropathy, and retinopathy. In a 27 day study, Compound 1 showed statistically significant reduction in HbA1c level in db/db type 2 diabetic mice after chronic treatment. Table 9 below and FIG. 10 provide the level of HbA1c at 0 and 27 days in Diabetic control group and group after chronic treatment with the Compound 1. The effect was statistically significant even when compared to semaglutide.

TABLE 9

Effect of treatment on % HbA1c levels in db/db mice

| Time Point | % HbA1c | | | | | | | | | | |
|---|---|---|---|---|---|---|---|---|---|---|---|
| | Diabetic Control (DC) | | | Compound 1 | | | | Semaglutide | | | |
| (Days) | Mean | SD | n | Mean | SD | n | % Change vs DC | Mean | SD | n | % Change vs DC |
| 0 | 4.70 | 0.52 | 6 | 4.87 | 0.59 | 6 | — | 5.05 | 0.35 | 5 | — |
| 27 | 7.30 | 1.17 | 6 | 3.73***## | 0.86 | 6 | −3.57 | 5.03*** | 0.69 | 5 | −2.26 |

*p < 0.05, p < 0.01, *p < 0.001 vs Diabetic Control; two way ANOVA followed by Bonferroni's posttests
#p < 0.05, ##p < 0.01, ###p < 0.001 vs Semaglutide; one way ANOVA followed by Bonferroni's posttests In a separate study, test Compound 1, 13 and 16 were studied and compared with semaglutide for their effect on HbA1c & insulin level and cumulative food consumption, body weight change and blood glucose AUC. The study was performed in similar manner as above on diabetic mouse model. The animals were divided into three treatment groups—a diabetic control group, a test group and a semaglutide treatment group. The representative compounds of the present disclosure, Compound 1, Compound 13 and Compound 16, were injected subcutaneously at 3.04 or 6.078 nM dose (every alternate day up to day 28 (q2d*15). The same dosage regimen was administered in semaglutide treatment group. Measurements of blood glucose levels and body weight were done daily. % HbA1c, Insulin was measured on Day 0, day 14 and day 29. Cumulative food intake and body weight change was calculated on day 14 and 29. % HbA1c, Insulin data was analyzed by two way ANOVA followed by Bonferroni's posttests using PRISM (Graph Pad version 5.03). Whereas Blood Glucose AUC, Body weight change and Cumulative food intake data was analyzed by one way ANOVA followed by Bonferroni's posttests using PRISM (Graph Pad version 5.03). From day 29 to day 45, animals were kept on recovery period during which no drug treatment was given. Blood Glucose and Body weight was measured during this period. On day 45, Body weight Changes, % HbA1c, Insulin was measured.

The results are provided in Tables 10, 11 and 12 below.

TABLE 10

HbA1C (%): Compound 1 (6.078 nM), Compound 13 (3.04 & 6.078 nM), Compound 16 (3.04 & 6.078 nM); (q2d*15) (n = 7)

| Time Point | % HbA1C | | | | | | | | | | | | | |
|---|---|---|---|---|---|---|---|---|---|---|---|---|---|---|
| | Diabetic Control (DC) | | Compound 1, 6.078 nM, q2d*15 | | Compound 13, 3.04 nM, q2d*15 | | Compound 13, 6.078 nM, q2d*15 | | Compound 16, 3.04 nM, q2d*15 | | Compound 16, 6.078 nM, q2d*15 | | Semaglutide, 12.15 nM, q2d*15 | |
| (Days) | Mean | SD | Mean | SD | Mean | SD | Mean | SD | Mean | SD | Mean | SD | Mean | SD |
| 0 | 7.7 | 1.2 | 7.8 | 0.8 | 7.7 | 1.5 | 7.83 | 0.76 | 7.74 | 1.27 | 7.83 | 0.99 | 7.66 | 1.13 |
| 14 | 8.0 | 1.0 | 6.4** | 0.5 | 6.6* | 0.9 | 6.00*** | 0.53 | 5.67***# | 0.68 | 5.64***# | 0.49 | 7.04 | 1.15 |
| 29 | 8.3 | 1.0 | 6.2*** | 0.5 | 6.4*** | 0.8 | 5.64*** | 0.51 | 5.33***# | 0.39 | 5.16***# | 0.24 | 6.47*** | 1.03 |

* = p < 0.05,  = p < 0.01, * = p < 0.001 vs. Diabetic Control, #p < 0.05, ##p < 0.01, ###p < 0.001 vs Semaglutide; One way ANOVA followed by Bonferroni's posttests

TABLE 11

Insulin (ng/mL): Compound 1 (6.078 nM), Compound 13 (3.04 &6.078 nM), Compound 16 (3.04 & 6.078 nM); (q2d*15) (n = 7)

| Time Point | Insulin (ng/mL) | | | | | | | | | | | | | |
|---|---|---|---|---|---|---|---|---|---|---|---|---|---|---|
| | Diabetic Control | | Compound 1, 6.078 nM, q2d*15 | | Compound 13, 3.04 nM, q2d*15 | | Compound 13, 6.078 nM, q2d*15 | | Compound 16, 3.04 nM, q2d*15 | | Compound 16, 6.078 nM, q2d*15 | | Sema, 12.15 nM, q2d*15 | |
| (Days) | Mean | SD | Mean | SD | Mean | SD | Mean | SD | Mean | SD | Mean | SD | Mean | SD |
| 0 | 17.6 | 5.5 | 18.0 | 5.8 | 21.7 | 12.1 | 26.2 | 14.0 | 13.9 | 6.6 | 21.8 | 9.6 | 18.7 | 10.3 |
| 14 | 23.0 | 10.7 | 58.1** | 31.6 | 41.8 | 28.2 | 61.2*** | 23.7 | 50.8* | 27.7 | 58.1** | 12.5 | 37.5 | 26.5 |
| 29 | 16.9 | 6.6 | 54.7** | 6.4 | 54.4** | 27.0 | 59.4*** | 22.4 | 53.8** | 23.5 | 68.2*** | 27.1 | 48.1** | 25.3 |

TABLE 11-continued

Insulin (ng/mL): Compound 1 (6.078 nM), Compound 13 (3.04 &6.078 nM), Compound 16 (3.04 & 6.078 nM); (q2d*15) (n = 7)

| Time Point | Insulin (ng/mL) | | | | | | | | | | | | | |
|---|---|---|---|---|---|---|---|---|---|---|---|---|---|---|
| | Diabetic Control | | Compound 1, 6.078 nM, q2d*15 | | Compound 13, 3.04 nM, q2d*15 | | Compound 13, 6.078 nM, q2d*15 | | Compound 16, 3.04 nM, q2d*15 | | Compound 16, 6.078 nM, q2d*15 | | Sema, 12.15 nM, q2d*15 | |
| (Days) | Mean | SD | Mean | SD | Mean | SD | Mean | SD | Mean | SD | Mean | SD | Mean | SD |

* = p < 0.05,  = p < 0.01, * = p < 0.001 vs Diabetic Control, #p < 0.05, ##p < 0.01, ###p < 0.001 vs Semaglutide; One way ANOVA followed by Bonferroni posttests

TABLE 12

Cumulative food Consumption, Blood Glucose $AUC_{(mg/dL*days)}$ and Body Weight Changes: Compound 1 (6.078 nM), Compound 13 (3.04 & 6.078 nM), Compound 16 (3.04 & 6.078 nM); (q2d*15)

| | Cumulative Food Intake (g) | | Blood Glucose AUC (Day 0-29) (mg/dL*days) | | | Body Weight Change Day 29, | |
|---|---|---|---|---|---|---|---|
| | Day 0-29 | | | | % Change Vs | % Change vs Day 0 | |
| Groups (n = 7) | Mean | SD | Mean | SD | Control | Mean | SD |
| Diabetic Control | 99.3 | 37.16 | 16948.1 | 281.48 | | 9.4 | 6.4 |
| Compound 1, 6.078 nM | 79.8 | 25.09 | 9194.6*** | 450.84 | −45.75 | −0.3 | 2.2 |
| Compound 13, 3.04 nM | 75.2 | 18.45 | 9515.4*** | 805.21 | −43.86 | 1.2 | 3.8 |
| Compound 13, 6.078 nM | 70.4 | 10.85 | 8451.7***## | 612.94 | −50.13 | −1.1 | 2.4 |
| Compound 16, 3.04 nM | 77.4 | 23.82 | 9399.0*** | 680.38 | −44.54 | −1.4 | 5.4 |
| Compound 16, 6.078 nM | 66.7 | 29.48 | 8086.1***## | 623.80 | −52.29 | −5.5 | 3.1 |
| Semaglutide, 12.155 nM | 92.0 | 6.64 | 9867.9*** | 832.73 | −41.78 | 0.7 | 3.9 |

* = p < 0.05,  = p < 0.01, * = p < 0.001 vs Diabetic Control, #p < 0.05, ##p < 0.01, ###p < 0.001 vs Semaglutide; One way ANOVA followed by Bonferroni posttests The representative compounds of the present disclosure (Compound 1, 13 and 16) at about 3 nM and 6 nM dose showed significant reduction in HbA1c, blood glucose, food consumption and body weight when compared to control (Table 12). The reduction was comparable to that shown by semaglutide at about 12 nM dose. Moreover, the effect was seen even after 29 days (Tables 13 and 14) which demonstrates the potential of compounds of present invention for developing long acting drug which do not require frequent administration and hence adding to the patient compliance.

TABLE 13

Recovery study-Blood Glucose $AUC_{(mg/dL*days)}$

| | Blood Glucose AUC (Day 30-37) (mg/dL*days) | | % Change | Blood Glucose AUC (Day 38-45) (mg/dL*days) | | % Change vs |
|---|---|---|---|---|---|---|
| Groups (n = 3) | Mean | SD | vs Control | Mean | SD | Control |
| Diabetic Control | 3591.7 | 47.04 | | 3601.7 | 38.66 | |
| Compound 1, 6.078 nM | 2787.3* | 17.67 | −22.39 | 3335.7 | 66.11 | −7.39 |
| Compound 13, 3.04 nM | 2588.7** | 411.97 | −27.93 | 3401.0 | 61.00 | −5.57 |
| Compound 13, 6.078 nM | 2875.7 | 436.87 | −19.94 | 3361.0 | 205.83 | −6.68 |
| Compound 16, 3.04 nM | 2420.0** | 89.71 | −32.62 | 3284.0* | 81.66 | −8.82 |
| Compound 16, 6.078 nM | 2167.7*** | 210.19 | −39.65 | 3134.7** | 103.39 | −12.97 |
| Semaglutide, 12.155 nM | 3032.0 | 182.40 | −15.58 | 3415.7 | 88.82 | −5.16 |

*p < 0.05, p < 0.01, *p < 0.001 vs Diabetic Control and #p < 0.05, ##p < 0.01, ###p < 0.001 vs Semaglutide; One Way ANOVA followed by Bonferroni's posttests

TABLE 14

| Recovery study-% HbA1C and Insulin (ng/mL) | | | | | | | |
|---|---|---|---|---|---|---|---|
| | % HbA1C | | Delta HbA1C vs | Insulin (ng/mL) | | Body Weight % Change vs Day 45 | |
| Groups (n = 3) | Mean | SD | DC | Mean | SD | Mean | SD |
| Diabetic Control | 8.5 | 0.4 | | 20.6 | 12.0 | 7.8 | 1.08 |
| Compound 1, 6.078 nM | 7.6 | 0.5 | −0.9 | 30.9 | 8.9 | 5.9 | 3.68 |
| Compound 13, 3.04 nM | 7.5 | 0.4 | −1.0 | 31.2 | 32.7 | 6.6 | 0.86 |
| Compound 13, 6.0788 nM | 7.3 | 0.4 | −1.2 | 34.3 | 12.4 | 5.5 | 2.19 |
| Compound 16, 3.04 nM | 7.1* | 0.2 | −1.4 | 15.5 | 8.2 | 6.1 | 0.38 |
| Compound 16, 6.078 nM | 7.2* | 0.5 | −1.3 | 18.4 | 18.7 | 5.7 | 0.36 |
| Semaglutide, 12.155 nM | 7.8 | 0.3 | −0.7 | 19.7 | 4.2 | 9.5 | 4.68 |

*p < 0.05, p < 0.01, *p < 0.001 vs Diabetic Control and #p < 0.05, ##p < 0.01, ###p < 0.001 vs Semaglutide; One Way ANOVA followed by Bonferroni's posttests These results demonstrate that the compound of present invention can find potential use for the treatment of diabetes and obesity.

We claim:
1. A polypeptide comprising the amino acid sequence:
(a)
(SEQ ID NO: 5)
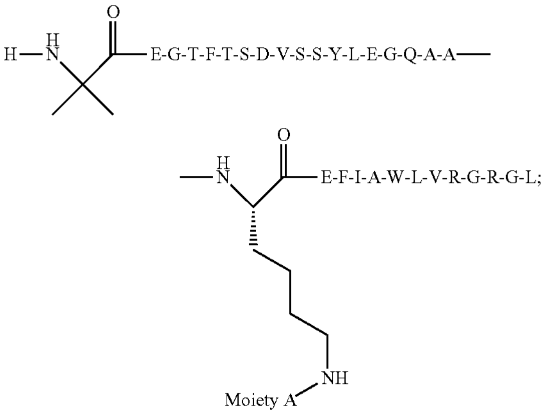
or
(b)
(SEQ ID NO: 6)
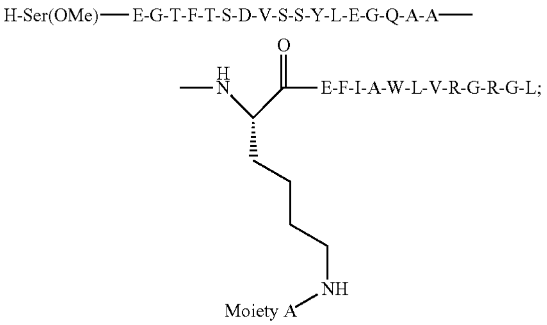
or
(c)
(SEQ ID NO: 7)
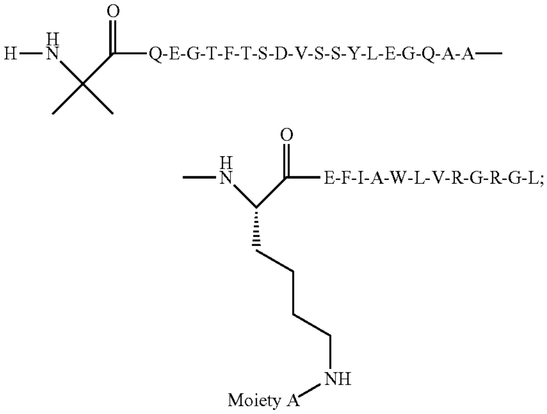
or
(d)
(SEQ ID NO: 8)
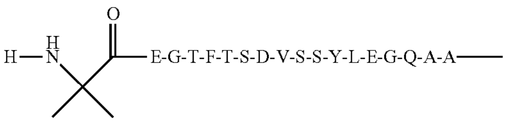
-continued
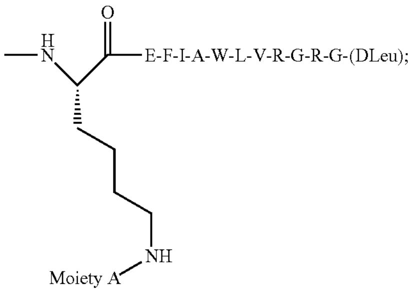
or
(e)
(SEQ ID NO: 9)
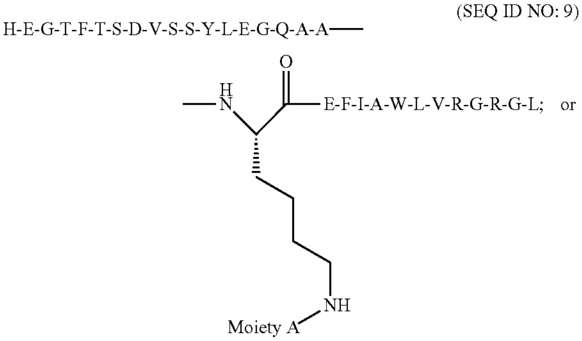
or
(f)
(SEQ ID NO: 10)
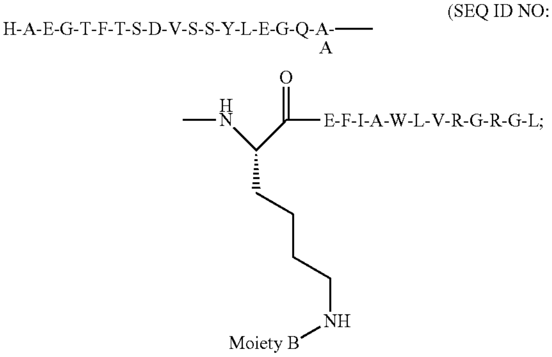
or
(g)
(SEQ ID NO: 5)
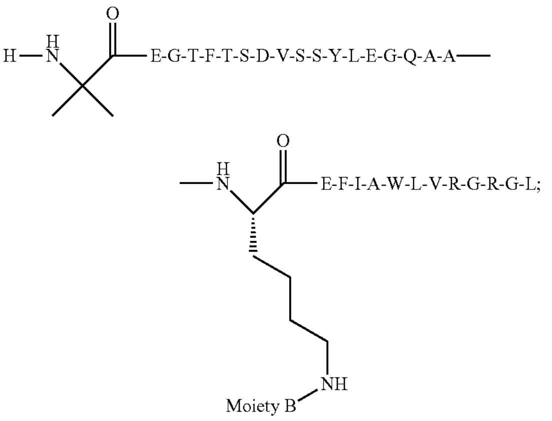
or

-continued
(h)
(SEQ ID NO: 11)
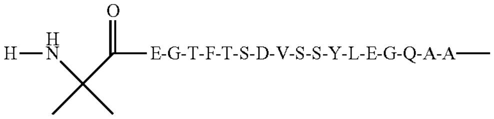
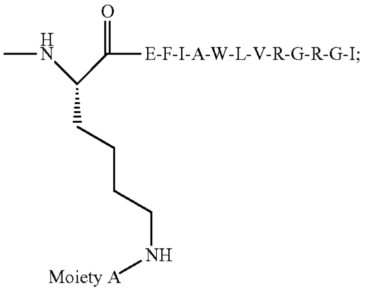
; or
(i)
(SEQ ID NO: 12)
H-(DSer(OMe))—E-G-T-F-T-S-D-V-S-S-Y-L-E-G-Q-A-A—
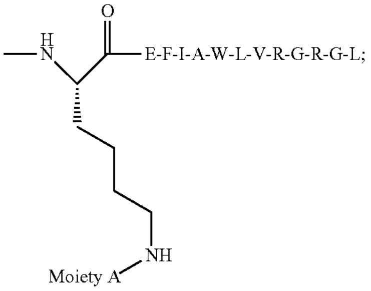
; or
(j)
(SEQ ID NO: 13)
H-(DSer)—E-G-T-F-T-S-D-V-S-S-Y-L-E-G-Q-A-A—
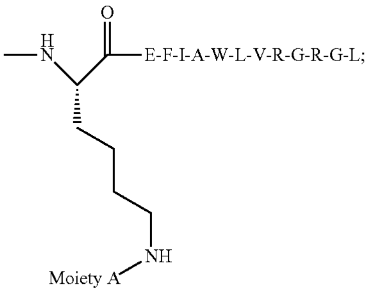
; or
(k)
(SEQ ID NO: 14)
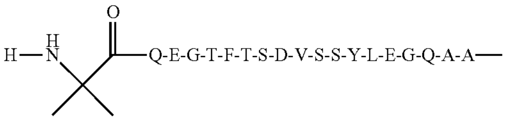
-continued
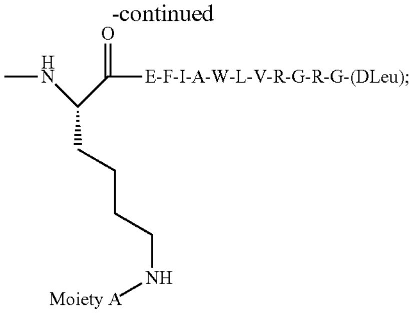
; or
(l)
(SEQ ID NO: 10)
H-A-E-G-T-F-T-S-D-V-S-S-Y-L-E-G-Q-A-A—
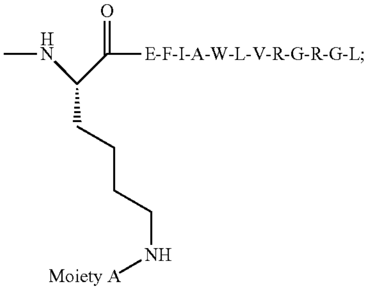
; or
(m)
(SEQ ID NO: 5)
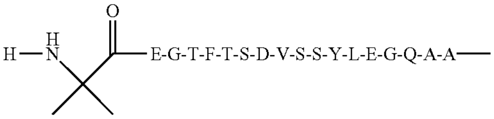
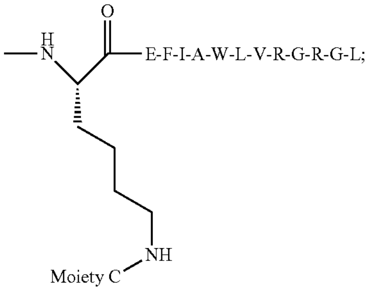
; or
(n)
(SEQ ID NO: 9)
H-S-E-G-T-F-T-S-D-V-S-S-Y-L-E-G-Q-A-A—
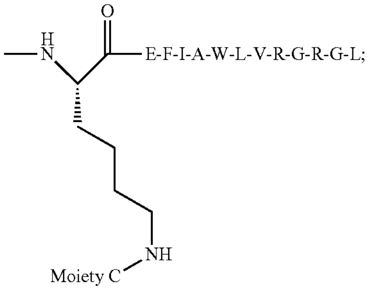
; or
(o)
(SEQ ID NO: 11)
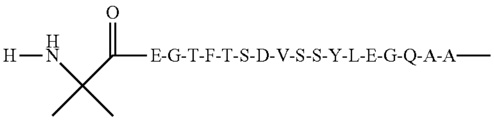

-continued

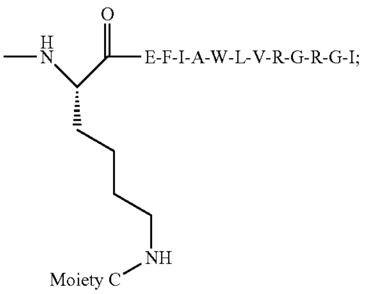

or (p)

(SEQ ID NO: 15)

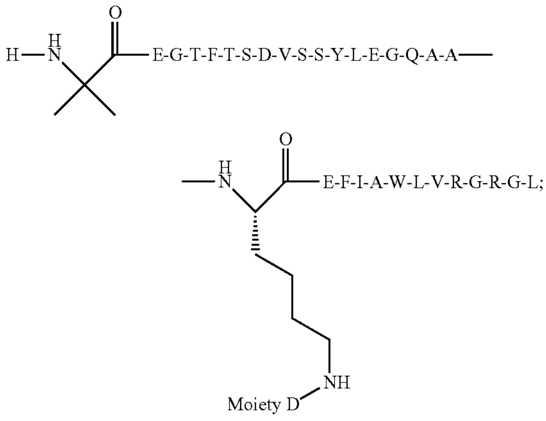

or (r)

(SEQ ID NO: 5)

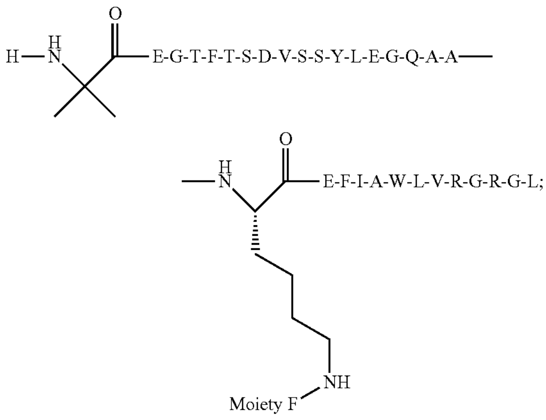

or wherein DSer is a serine residue having a D-configuration and DLeu is a leucine residue having a D-configuration;

wherein Ser(OMe) is a serine residue having the structure:

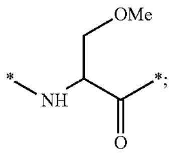

wherein Moiety A has the structure:

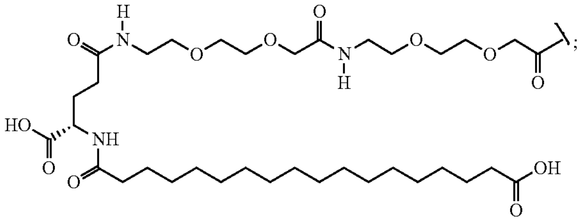 [SMILES: CC(=O)COCCOCCNC(=O)COCCOCCNC(=O)CC[C@H](NC(=O)CCCCCCCCCCCCCCCCC(=O)O)C(=O)O]

wherein Moiety B has the structure:

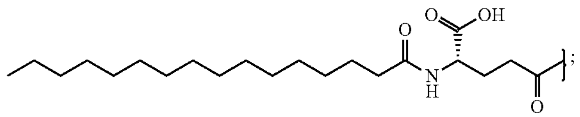 [SMILES: CCCCCCCCCCCCCCCC(=O)N[C@@H](CCC(C)=O)C(=O)O]

wherein Moiety C has the structure:

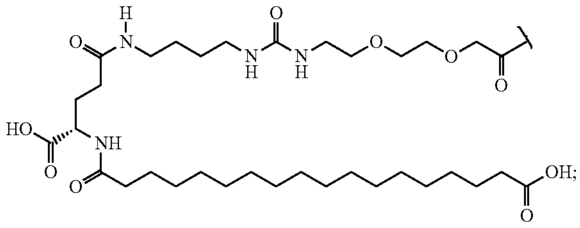 [SMILES: CC(=O)COCCOCCNC(=O)NCCCCNC(=O)CC[C@H](NC(=O)CCCCCCCCCCCCCCCCC(=O)O)C(=O)O]

wherein moiety D has the structure:

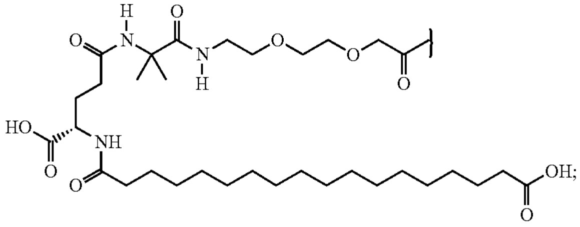 [SMILES: CC(=O)COCCOCCNC(=O)C(C)(C)NC(=O)CC[C@H](NC(=O)CCCCCCCCCCCCCCCCC(=O)O)C(=O)O]

wherein Moiety E has the structure:

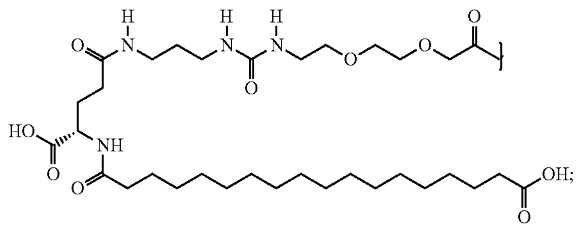

and and
wherein Moiety F has the structure:
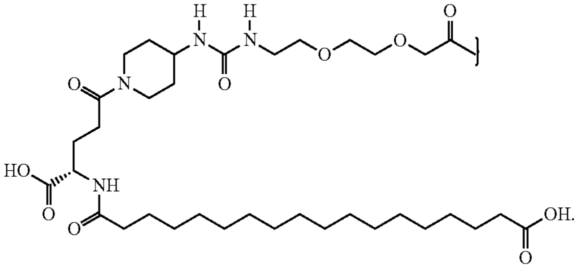 [SMILES: CC(=O)COCCOCCNC(=O)NC1CCN(C(=O)CC[C@H](NC(=O)CCCCCCCCCCCCCCCCC(=O)O)C(=O)O)CC1]
2. The polypeptide of claim 1, wherein the polypeptide comprises the amino acid sequence:
(SEQ ID NO: 5)
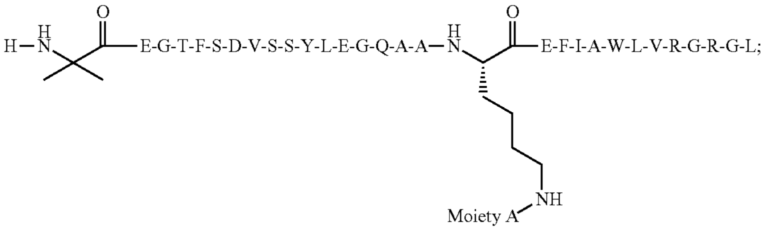
wherein Moiety A has the structure:
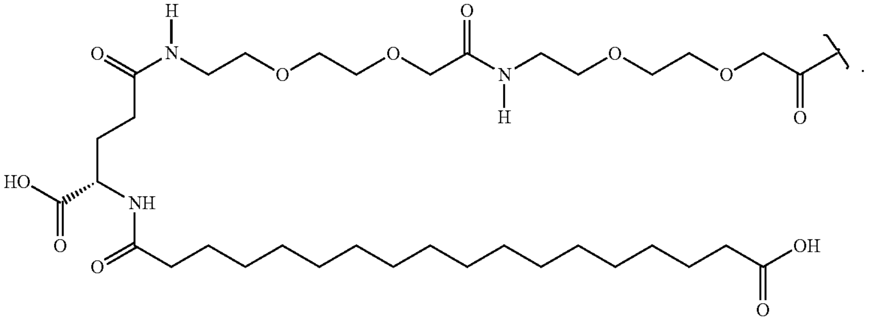 [SMILES: CC(=O)COCCOCCNC(=O)COCCOCCNC(=O)CC[C@H](NC(=O)CCCCCCCCCCCCCCCCC(=O)O)C(=O)O]
3. The polypeptide of claim 1, wherein the polypeptide comprises the amino acid sequence:
(SEQ ID NO: 6)
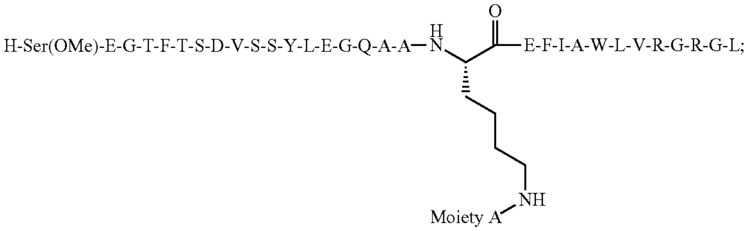

wherein Ser(OMe) is a serine residue having the structure:
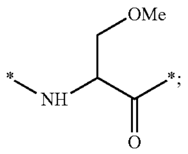
and
wherein Moiety A has the structure:
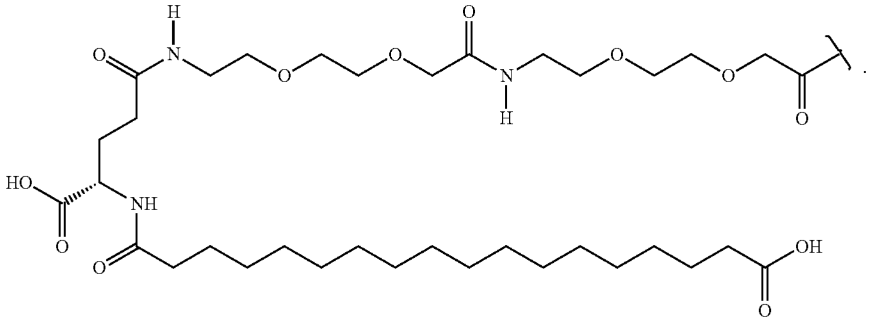 [SMILES: CC(=O)COCCOCCNC(=O)COCCOCCNC(=O)CC[C@H](NC(=O)CCCCCCCCCCCCCCCCC(=O)O)C(=O)O]
4. The polypeptide of claim 1, wherein the polypeptide comprises the amino acid sequence:
(SEQ ID NO: 7)
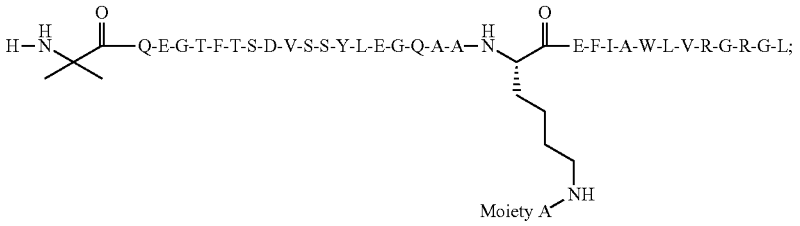
wherein Moiety A has the structure:
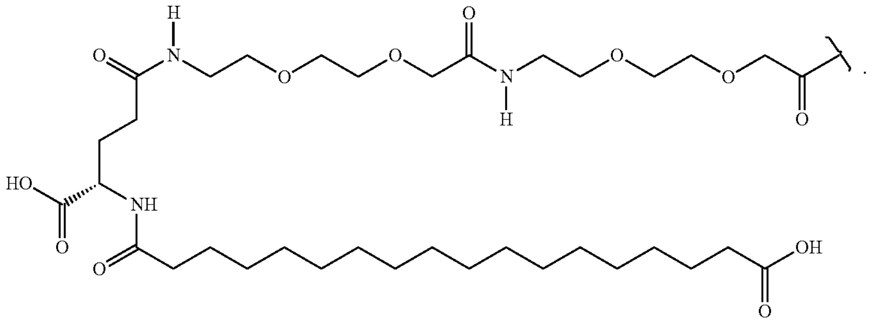 [SMILES: CC(=O)COCCOCCNC(=O)COCCOCCNC(=O)CC[C@H](NC(=O)CCCCCCCCCCCCCCCCC(=O)O)C(=O)O]

5. The polypeptide of claim 1, wherein the polypeptide comprises the amino acid sequence:
(SEQ ID NO: 8)
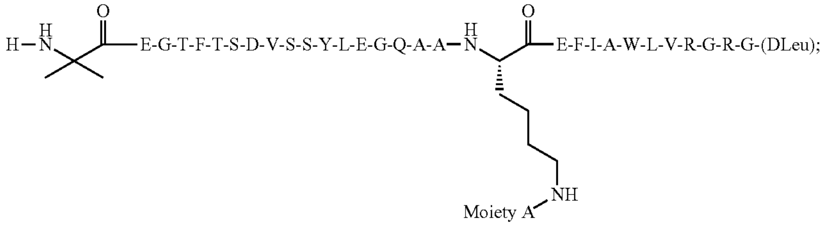
wherein DLeu is a leucine residue having a D-configuration; and
wherein Moiety A has the structure:
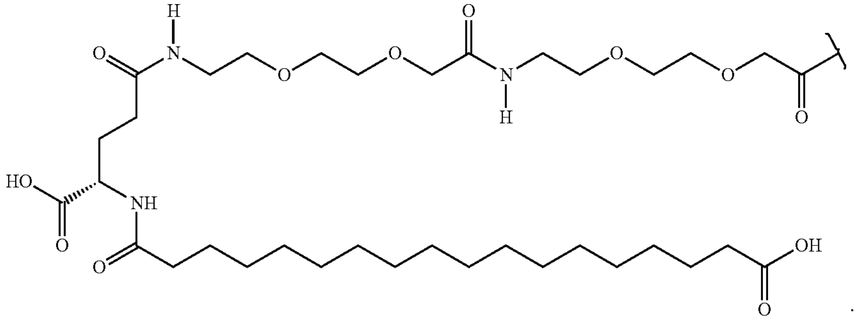 [SMILES: CC(=O)COCCOCCNC(=O)COCCOCCNC(=O)CC[C@H](NC(=O)CCCCCCCCCCCCCCCCC(=O)O)C(=O)O]
6. The polypeptide of claim 1, wherein the polypeptide comprises the amino acid sequence:
(SEQ ID NO: 9)
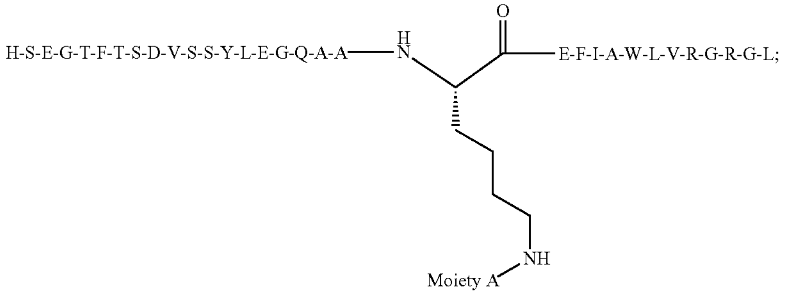

wherein Moiety A has the structure:
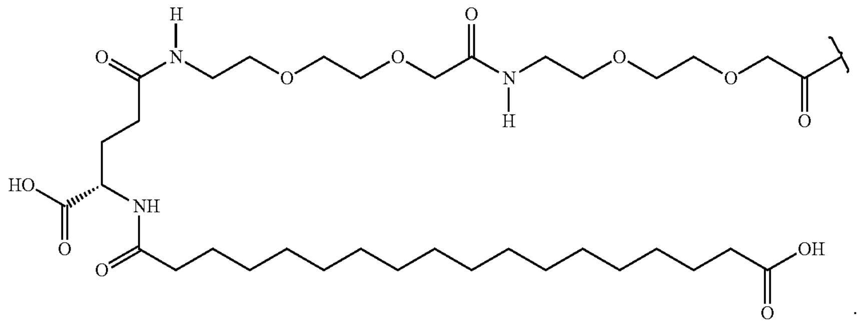 [SMILES: CC(=O)COCCOCCNC(=O)COCCOCCNC(=O)CC[C@H](NC(=O)CCCCCCCCCCCCCCCCC(=O)O)C(=O)O]
7. The polypeptide of claim 1, wherein the polypeptide comprises the amino acid sequence:
(SEQ ID NO:10)
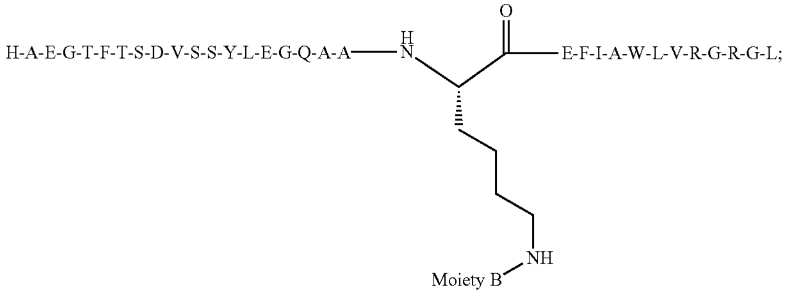
wherein Moiety B has the structure:
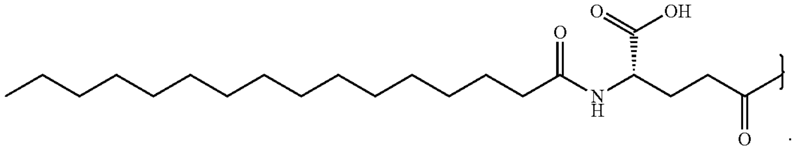 [SMILES: CCCCCCCCCCCCCCCC(=O)N[C@@H](CCC(C)=O)C(=O)O]
8. The polypeptide of claim 1, wherein the polypeptide comprises the amino acid sequence:
(SEQ ID NO: 5)
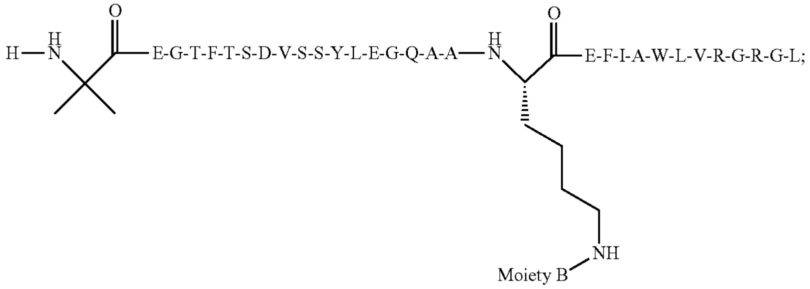

wherein Moiety B has the structure:
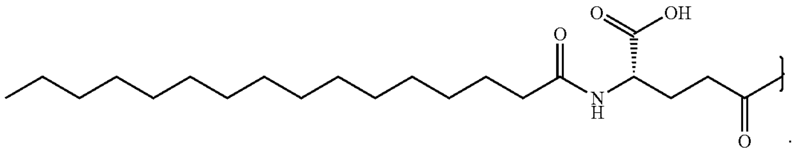 [SMILES: CCCCCCCCCCCCCCCC(=O)N[C@@H](CCC(C)=O)C(=O)O]
9. The polypeptide of claim 1, wherein the polypeptide comprises the amino acid sequence:
(SEQ ID NO: 11)
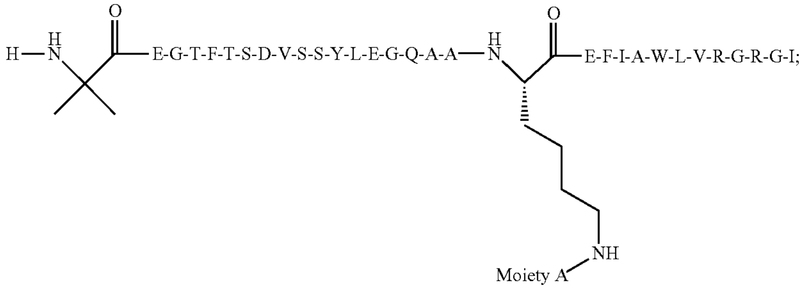
wherein Moiety A has the structure:
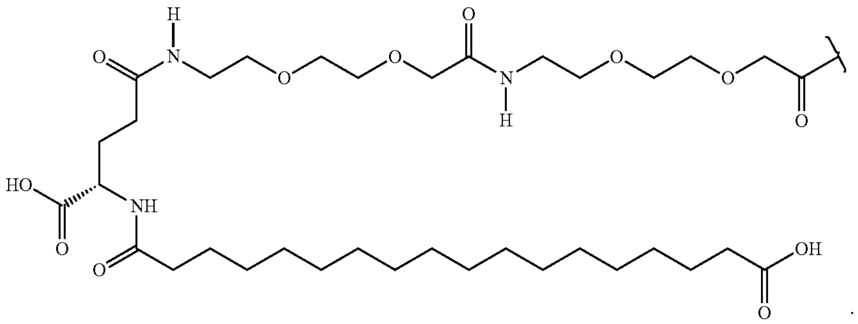 [SMILES: CC(=O)COCCOCCNC(=O)COCCOCCNC(=O)CC[C@H](NC(=O)CCCCCCCCCCCCCCCCC(=O)O)C(=O)O]
10. The polypeptide of claim 1, wherein the polypeptide comprises the amino acid sequence:
(SEQ ID NO: 12)
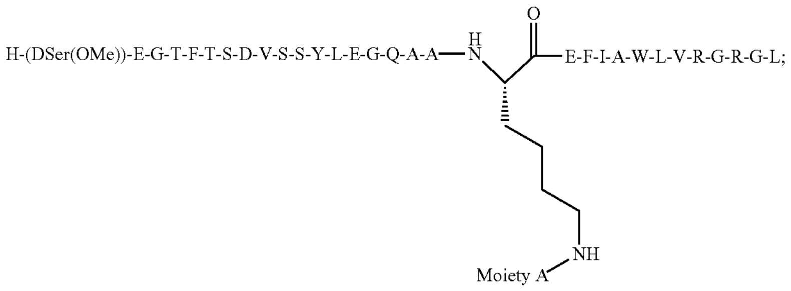

wherein DSer is a serine residue having a D-configuration and DLeu is a leucine residue having a D-configuration;

wherein Ser(OMe) is a serine residue having the structure:

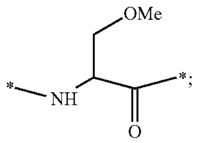

and wherein Moiety A has the structure:

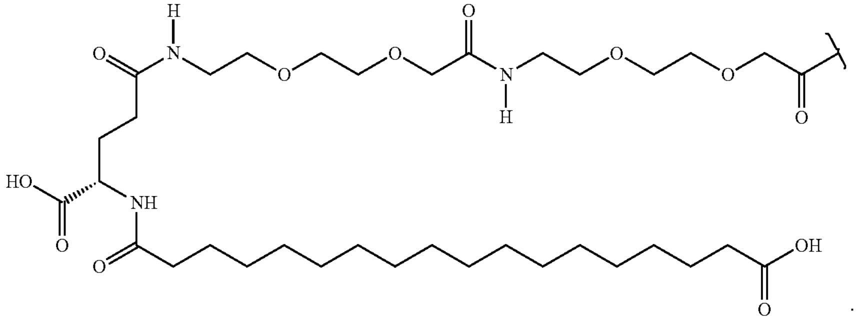 [SMILES: CC(=O)COCCOCCNC(=O)COCCOCCNC(=O)CC[C@H](NC(=O)CCCCCCCCCCCCCCCCC(=O)O)C(=O)O]

11. The polypeptide of claim 1, wherein the polypeptide comprises the amino acid sequence:

(SEQ ID NO: 13)

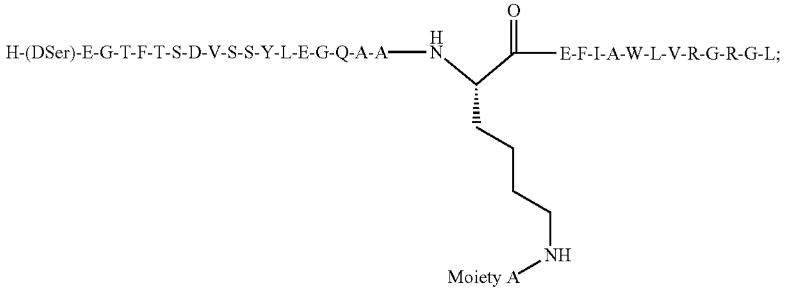

wherein DSer is a serine residue having a D-configuration; and wherein Moiety A has the structure:

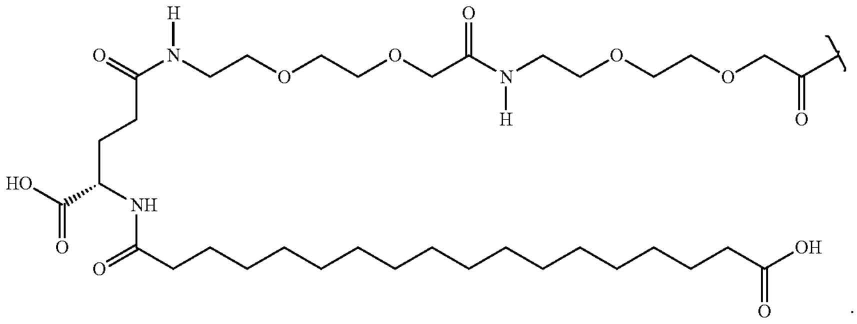 [SMILES: CC(=O)COCCOCCNC(=O)COCCOCCNC(=O)CC[C@H](NC(=O)CCCCCCCCCCCCCCCCC(=O)O)C(=O)O]

12. The polypeptide of claim 1, wherein the polypeptide comprises the amino acid sequence:
(SEQ ID NO: 14)
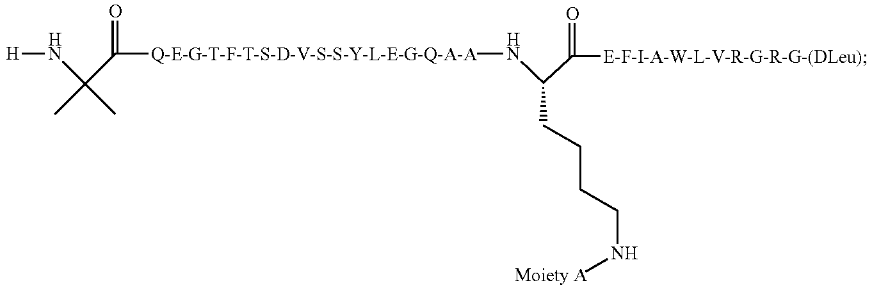
wherein DLeu is a leucine residue having a D-configuration; and
wherein Moiety A has the structure:
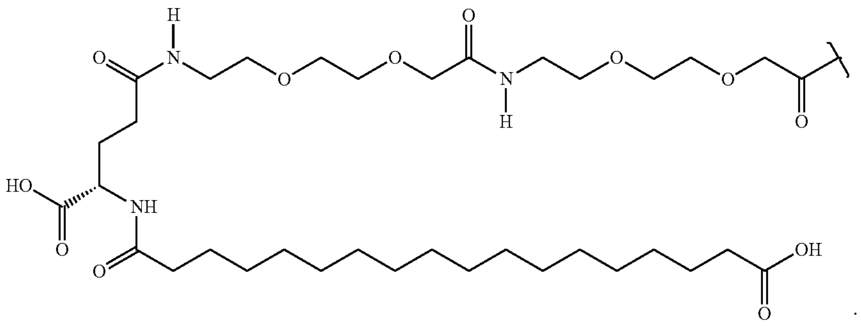 [SMILES: CC(=O)COCCOCCNC(=O)COCCOCCNC(=O)CC[C@H](NC(=O)CCCCCCCCCCCCCCCCC(=O)O)C(=O)O]
13. The polypeptide of claim 1, wherein the polypeptide comprises the amino acid sequence:
(SEQ ID NO: 10)
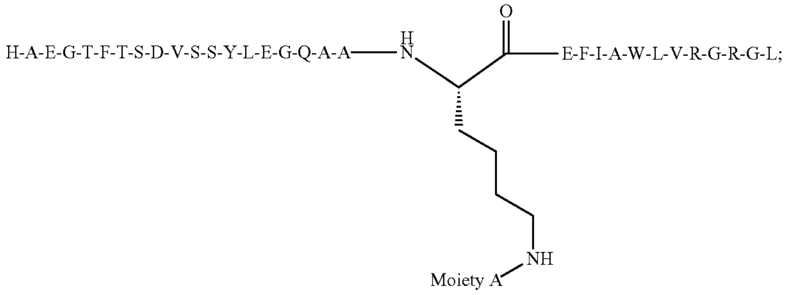

wherein Moiety A has the structure:
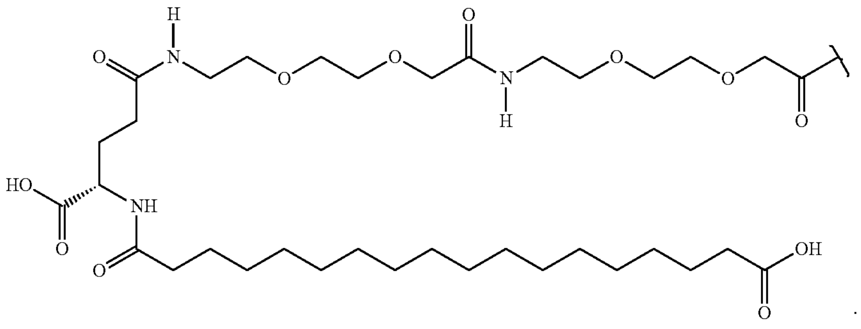 [SMILES: CC(=O)COCCOCCNC(=O)COCCOCCNC(=O)CC[C@H](NC(=O)CCCCCCCCCCCCCCCCC(=O)O)C(=O)O]
14. The polypeptide of claim 1, wherein the polypeptide comprises the amino acid sequence:
(SEQ ID NO: 5)
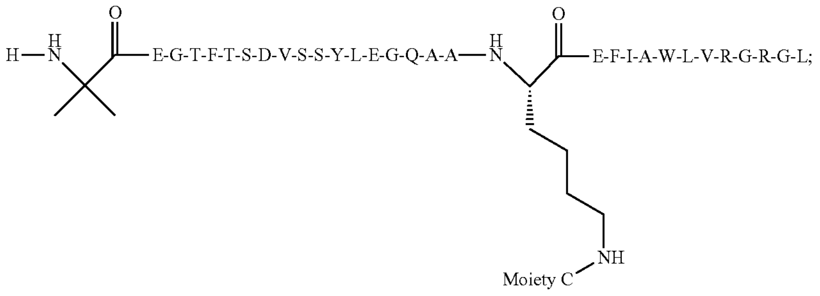
wherein Moiety C has the structure:
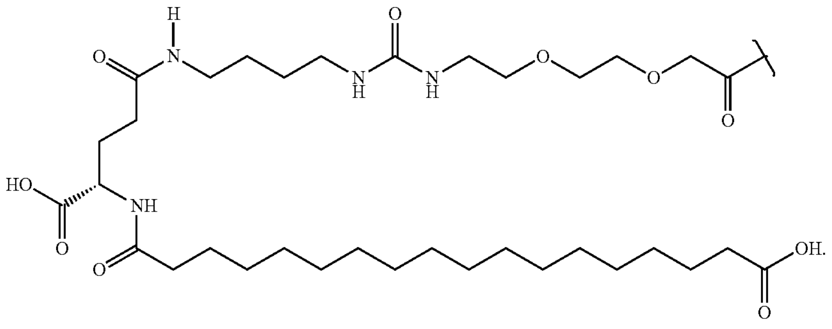 [SMILES: CC(=O)COCCOCCNC(=O)NCCCCNC(=O)CC[C@H](NC(=O)CCCCCCCCCCCCCCCCC(=O)O)C(=O)O]

15. The polypeptide of claim 1, wherein the polypeptide comprises the amino acid sequence:
(SEQ ID NO: 9)
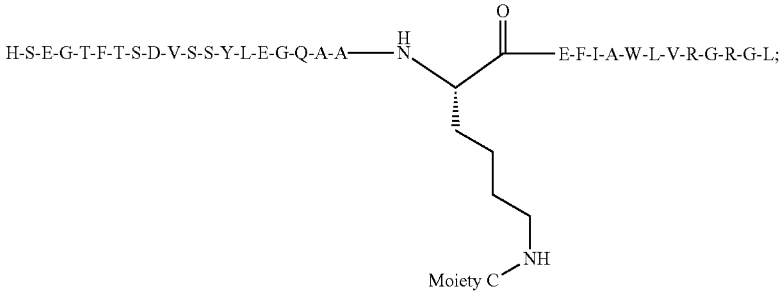
wherein Moiety C has the structure:
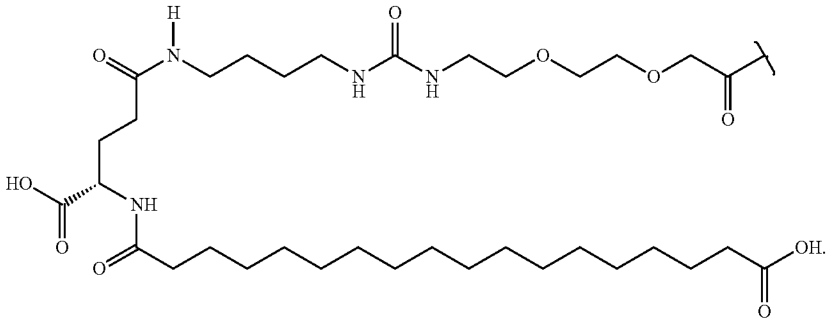 [SMILES: CC(=O)COCCOCCNC(=O)NCCCCNC(=O)CC[C@H](NC(=O)CCCCCCCCCCCCCCCCC(=O)O)C(=O)O]
16. The polypeptide of claim 1, wherein the polypeptide comprises the amino acid sequence:
(SEQ ID NO: 11)
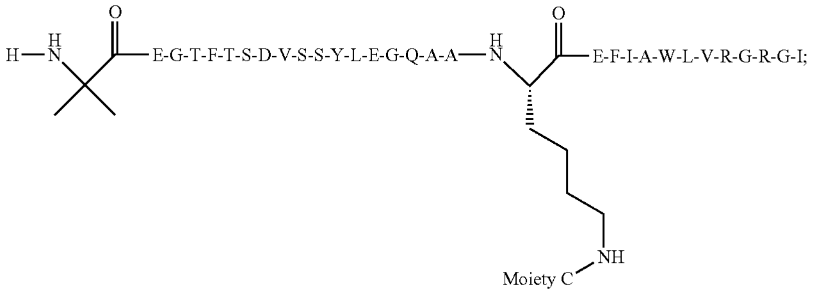

wherein Moiety C has the structure:
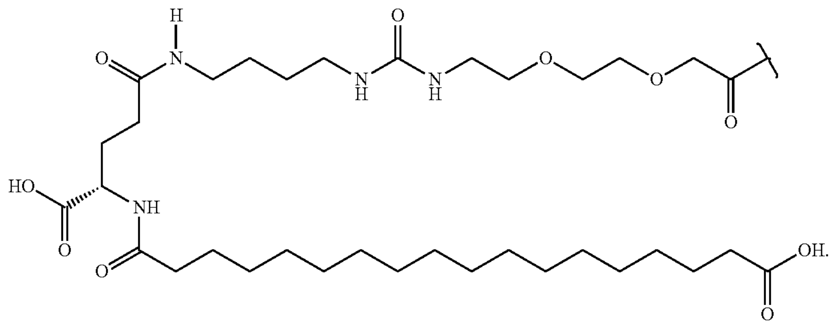 [SMILES: CC(=O)COCCOCCNC(=O)NCCCCNC(=O)CC[C@H](NC(=O)CCCCCCCCCCCCCCCCC(=O)O)C(=O)O]
17. The polypeptide of claim 1, wherein the polypeptide comprises the amino acid sequence:
(SEQ ID NO: 5)
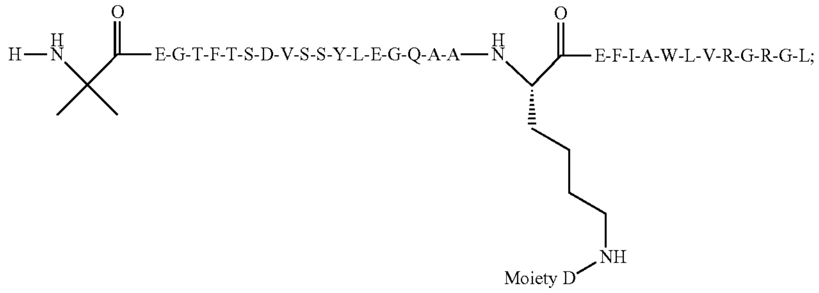
wherein Moiety D has the structure:
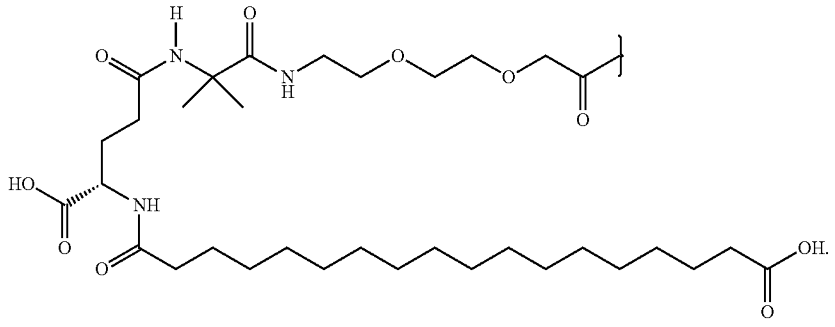 [SMILES: CC(=O)COCCOCCNC(=O)C(C)(C)NC(=O)CC[C@H](NC(=O)CCCCCCCCCCCCCCCCC(=O)O)C(=O)O]

18. The polypeptide of claim 1, wherein the polypeptide comprises the amino acid sequence:
(SEQ ID NO: 5)
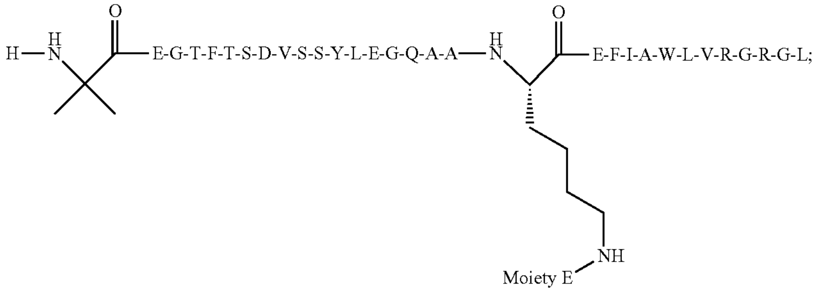
wherein Moiety E has the structure:
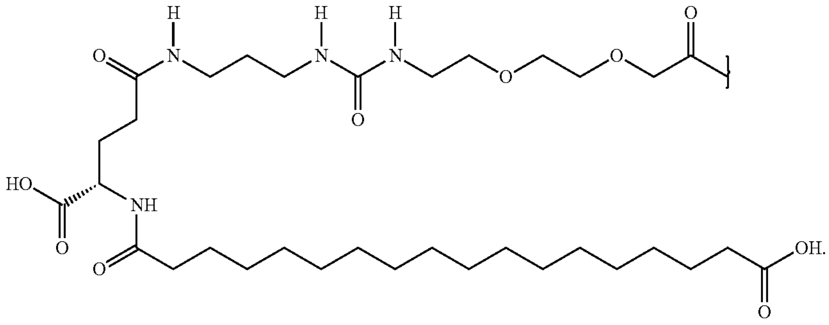 [SMILES: CC(=O)COCCOCCNC(=O)NCCCNC(=O)CC[C@H](NC(=O)CCCCCCCCCCCCCCCCC(=O)O)C(=O)O]
19. The polypeptide of claim 1, wherein the polypeptide comprises the amino acid sequence:
(SEQ ID NO: 5)
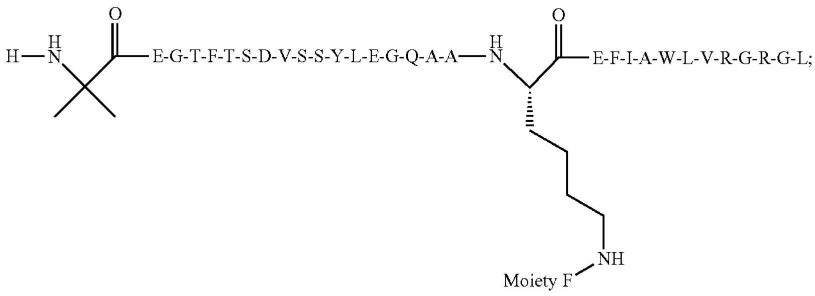

wherein Moiety F has the structure:
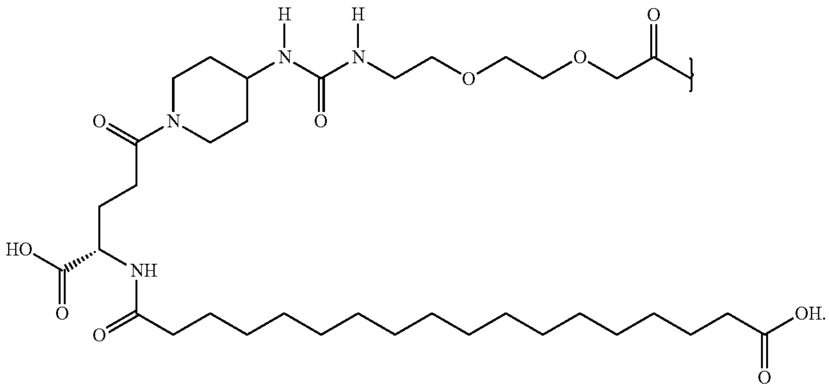 [SMILES: CC(=O)COCCOCCNC(=O)NC1CCN(C(=O)CC[C@H](NC(=O)CCCCCCCCCCCCCCCCC(=O)O)C(=O)O)CC1]
* * * * *

SEQUENCE LISTING

```
<160> NUMBER OF SEQ ID NOS: 14

<210> SEQ ID NO 1
<211> LENGTH: 31
<212> TYPE: PRT
<213> ORGANISM: Homo sapiens
<220> FEATURE:
<221> NAME/KEY: MISC_FEATURE
<223> OTHER INFORMATION: Native GLP-1 (7-37)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 2
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Liraglutide
<220> FEATURE:
<221> NAME/KEY: MISC_FEATURE
<222> LOCATION: (20)..(20)
<223> OTHER INFORMATION: Lys is substituted

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30


<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Semaglutide
<220> FEATURE:
<221> NAME/KEY: MISC_FEATURE
<222> LOCATION: (2)..(2)
<223> OTHER INFORMATION: Xaa= Aib
```

```
<220> FEATURE:
<221> NAME/KEY: MISC_FEATURE
<222> LOCATION: (20)..(20)
<223> OTHER INFORMATION: Lys is substituted

<400> SEQUENCE: 3

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30


<210> SEQ ID NO 4
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=  Ser, Ser(OMe), D-Ser, D-Ser(OMe), Ala or
      Aib
<220> FEATURE:
<221> NAME/KEY: MISC_FEATURE
<222> LOCATION: (3)..(3)
<223> OTHER INFORMATION: Xaa=  Absent or Gln
<220> FEATURE:
<221> NAME/KEY: MISC_FEATURE
<222> LOCATION: (4)..(4)
<223> OTHER INFORMATION: Xaa=  Glu
<220> FEATURE:
<221> NAME/KEY: MISC_FEATURE
<222> LOCATION: (16)..(16)
<223> OTHER INFORMATION: Xaa=  Glu
<220> FEATURE:
<221> NAME/KEY: MISC_FEATURE
<222> LOCATION: (21)..(21)
<223> OTHER INFORMATION: Lys is substituted
<220> FEATURE:
<221> NAME/KEY: MISC_FEATURE
<222> LOCATION: (24)..(24)
<223> OTHER INFORMATION: Xaa=  Ile
<220> FEATURE:
<221> NAME/KEY: MISC_FEATURE
<222> LOCATION: (33)..(33)
<223> OTHER INFORMATION: Xaa=  Leu, D-Leu, D-Ile or Ile
<220> FEATURE:
<221> NAME/KEY: MISC_FEATURE
<222> LOCATION: (34)..(34)
<223> OTHER INFORMATION: Xaa=  Absent

<400> SEQUENCE: 4

His Xaa Xaa Xaa Gly Thr Phe Thr Ser Asp Val Ser Ser Tyr Leu Xaa
1               5                   10                  15

Gly Gln Ala Ala Xaa Glu Phe Xaa Ala Trp Leu Val Arg Gly Arg Gly
            20                  25                  30

Xaa Xaa


<210> SEQ ID NO 5
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(20)
<223> OTHER INFORMATION: Lys is substituted
```

<400> SEQUENCE: 5

His Xaa Glu Gly Thr Phe Thr Ser Asp Val Ser Ser Tyr Leu Glu Gly
1 5 10 15

Gln Ala Ala Lys Glu Phe Ile Ala Trp Leu Val Arg Gly Arg Gly Leu
20 25 30

<210> SEQ ID NO 6
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa= Ser(OMe)
<220> FEATURE:
<221> NAME/KEY: MISC_FEATURE
<222> LOCATION: (20)..(20)
<223> OTHER INFORMATION: Lys is substituted

<400> SEQUENCE: 6

His Xaa Glu Gly Thr Phe Thr Ser Asp Val Ser Ser Tyr Leu Glu Gly
1 5 10 15

Gln Ala Ala Lys Glu Phe Ile Ala Trp Leu Val Arg Gly Arg Gly Leu
20 25 30

<210> SEQ ID NO 7
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (21)..(21)
<223> OTHER INFORMATION: Lys is substituted

<400> SEQUENCE: 7

His Xaa Gln Glu Gly Thr Phe Thr Ser Asp Val Ser Ser Tyr Leu Glu
1 5 10 15

Gly Gln Ala Ala Lys Glu Phe Ile Ala Trp Leu Val Arg Gly Arg Gly
20 25 30

Leu

<210> SEQ ID NO 8
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(20)
<223> OTHER INFORMATION: Lys is substituted
<220> FEATURE:
<221> NAME/KEY: MISC_FEATURE
<222> LOCATION: (32)..(32)
<223> OTHER INFORMATION: Xaa= D-Leu

<400> SEQUENCE: 8

His Xaa Glu Gly Thr Phe Thr Ser Asp Val Ser Ser Tyr Leu Glu Gly
1 5 10 15

Gln Ala Ala Lys Glu Phe Ile Ala Trp Leu Val Arg Gly Arg Gly Xaa
20 25 30

<210> SEQ ID NO 9
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: Lys is substituted

<400> SEQUENCE: 9

His Ser Glu Gly Thr Phe Thr Ser Asp Val Ser Ser Tyr Leu Glu Gly
1 5 10 15

Gln Ala Ala Lys Glu Phe Ile Ala Trp Leu Val Arg Gly Arg Gly Leu
20 25 30

<210> SEQ ID NO 10
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: Lys is substituted

<400> SEQUENCE: 10

His Ala Glu Gly Thr Phe Thr Ser Asp Val Ser Ser Tyr Leu Glu Gly
1 5 10 15

Gln Ala Ala Lys Glu Phe Ile Ala Trp Leu Val Arg Gly Arg Gly Leu
20 25 30

<210> SEQ ID NO 11
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(20)
<223> OTHER INFORMATION: Lys is substituted

<400> SEQUENCE: 11

His Xaa Glu Gly Thr Phe Thr Ser Asp Val Ser Ser Tyr Leu Glu Gly
1 5 10 15

Gln Ala Ala Lys Glu Phe Ile Ala Trp Leu Val Arg Gly Arg Gly Ile
20 25 30

<210> SEQ ID NO 12
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Ser(OMe)
<220> FEATURE:
<221> NAME/KEY: MISC_FEATURE
<222> LOCATION: (20)..(20)
<223> OTHER INFORMATION: Lys is substituted

<400> SEQUENCE: 12

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Leu
            20                  25                  30
```

<210> SEQ ID NO 13
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Ser
<220> FEATURE:
<221> NAME/KEY: MISC_FEATURE
<222> LOCATION: (20)..(20)
<223> OTHER INFORMATION: Lys is substituted

<400> SEQUENCE: 13

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Leu
            20                  25                  30
```

<210> SEQ ID NO 14
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (21)..(21)
<223> OTHER INFORMATION: Lys is substituted
<220> FEATURE:
<221> NAME/KEY: MISC_FEATURE
<222> LOCATION: (33)..(33)
<223> OTHER INFORMATION: Xaa = D-Leu

<400> SEQUENCE: 14

```
His Xaa Gln Glu Gly Thr Phe Thr Ser Asp Val Ser Ser Tyr Leu Glu
1               5                   10                  15

Gly Gln Ala Ala Lys Glu Phe Ile Ala Trp Leu Val Arg Gly Arg Gly
            20                  25                  30

Xaa
```

UNITED STATES PATENT AND TRADEMARK OFFICE
CERTIFICATE OF CORRECTION

PATENT NO. : 11,242,373 B2  
APPLICATION NO. : 16/985207  
DATED : February 8, 2022  
INVENTOR(S) : Rajamannar Thennati et al.

Page 1 of 1

It is certified that error appears in the above-identified patent and that said Letters Patent is hereby corrected as shown below:

In the Claims

In Claim 1, at Column 57, Line 32, in between compound (p) and (r) please add the following:

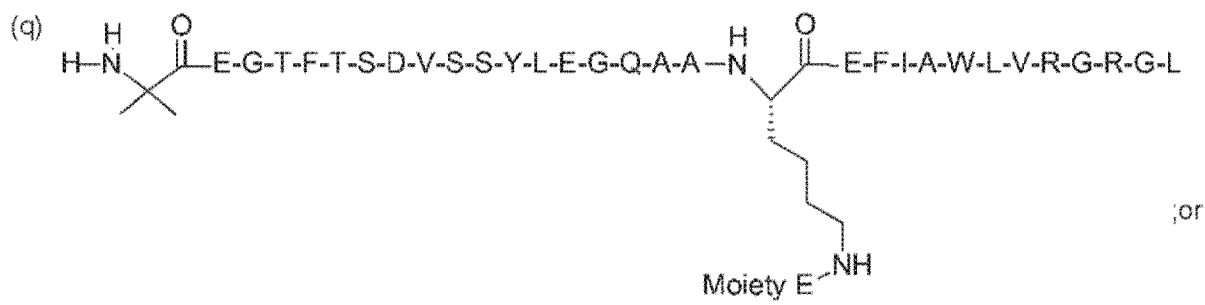

Signed and Sealed this  
Second Day of May, 2023

Katherine Kelly Vidal  
*Director of the United States Patent and Trademark Office*